US008691764B2

(12) United States Patent
Zhang et al.

(10) Patent No.: US 8,691,764 B2
(45) Date of Patent: Apr. 8, 2014

(54) INHIBITORS OF NF-κB ACTIVITY

(75) Inventors: Zhiquan Zhang, Durham, NC (US); Basil Rigas, Old Field, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 836 days.

(21) Appl. No.: 12/593,550

(22) PCT Filed: Mar. 28, 2008

(86) PCT No.: PCT/US2008/058759
§ 371 (c)(1),
(2), (4) Date: Apr. 5, 2010

(87) PCT Pub. No.: WO2008/121881
PCT Pub. Date: Oct. 9, 2008

(65) Prior Publication Data
US 2012/0004175 A1    Jan. 5, 2012

Related U.S. Application Data

(60) Provisional application No. 60/907,314, filed on Mar. 28, 2007.

(51) Int. Cl.
| A61K 38/00 | (2006.01) |
| A61P 29/00 | (2006.01) |
| C12N 15/00 | (2006.01) |
| C12N 5/00 | (2006.01) |
| C12N 5/02 | (2006.01) |
| A61P 23/00 | (2006.01) |
| A61P 35/00 | (2006.01) |

(52) U.S. Cl.
USPC ...... 514/12.2; 435/320.1; 435/375; 514/18.3; 514/19.2

(58) Field of Classification Search
None
See application file for complete search history.

(56) References Cited

U.S. PATENT DOCUMENTS

| 6,858,579 B2 * | 2/2005 | Perritti et al. ................. 514/16.4 |
| 2003/0215528 A1 * | 11/2003 | Graham et al. ................ 424/718 |
| 2006/0013802 A1 * | 1/2006 | Shafer .......................... 424/85.2 |

OTHER PUBLICATIONS

Kamal et al. An annexin 1 (ANXA1)-derived peptide inhibits prototype antigen-driven human T cell Th1 and Th2 responses in vitro. Clinical and Experimental Allergy, 2001, vol. 31, pp. 1116-1125.*
Bandeira-Melo et al. A novel effect for annexin 1-derived peptide ac2-26: reduction of allergic inflammation in the rat.J Pharmacol Exp Ther. Jun. 2005 and Epub Mar. 22, 2005, vol. 313, No. 3, pp. 1416-1422.*
Andrews, N.C., et al., "A rapid micropreparation technique for extraction of DNA-binding proteins from limiting numbers of mammalian cells"; Nucleic Acids. Res (1991); vol. 19:9; p. 2499.
Brody, E.N. et al., The Use of Aptamers in Large Arrays for Molecular Diagnostics:, Molecular Diagnosis (1999); vol. 4:4; pp. 381-388.
Campbell, K. et al., "Regulation of NF-κB Function", Biochem. Soc. Symp. (2006); vol. 73; pp. 165-180.
Cho, C. Y. et al., "Synthesis and Screening of Linear and Cyclic Oligocarbamate Libraries. Discovery of High Affinity Ligands for GPIIb/IIIa" J. Am. Chem. Soc.(1998); vol. 120:31; pp. 7706-7718.
Fahey, J.W., et al., "Antioxidant Functions of Sulforaphane: A Potent Inducer of Phase II Detoxication Enzymes", Food and Chemical Toxicology (1999); vol. 37; pp. 973-979.
Gao, J., et al., "Nitric Oxide-donating Aspirin Induces Apoptosis in Human Colon Cancer Through Induction of Oxidative Stress", PNAS (2005); vol. 102:47; pp. 17207-17212.
Gerke, V., et al., "Annexins: Linking Ca2+ Signalling to Membrane Dynamics", Nature Reviews Molecular Cell Biology (2005); vol. 6; pp. 449-461.
Griffith, O., et al., Potent and Specific Inhibition of Glutathione Synthesis by Buthionine Sulfoximine (S-n-Butyl Homocysteine Sulfoximine), J Biological Chemistry (1979); vol. 254:16; pp. 7558-7560.
Halliwell, B., "Oxidative Stress and Cancer: Have We Moved Forward?", Biochem (2007), vol. 401, pp. 1-11.
Hayes, M. J., et al., "Annexins and Disease", Biochemical and Biophysical Research Communication (2004); vol. 322; pp. 1166-1170.
Jayasena, S. D. "Aptamers: An Emerging Class of Molecules That Rival Antibodies in Diagnostics", Clinical Chemistry (1999); vol. 45:9; pp. 1628-1650.
Kamal, A. M., et al., "An Overview of the Effects of Annexin 1 on Cells Involved in the Inflammatory Process", Mem Inst Oswaldo Cruz, Rio de Janeiro (2005); vol. 100:Suppl.1; pp. 39-48.
Karin, K., "Nuclear Factor-κB in Cancer Development and Progression", Nature (2006); vol. 441; pp. 431-436.
Lipkin, M., et al., "Preclinical Mouse Models for Cancer Chemoprevention Studies" Ann NY Acad. Sci. (1999); vol. 889; pp. 14-19.
Moser, A. R., et al., "A Dominant Mutation That Predisposes to Multiple Intestinal Neoplasia in the Mouse" Science (1990), vol. 247, pp. 322-324.
Ouyang, N., et al., "Nitric Oxide-Donating Aspirin Prevents Pancreatic Cancer in a Hamster Tumor Model" Can. Res. (2006); vol. 66:8; pp. 4503-4511.
Perretti, M. et al., "Annexin 1 and the Biology of the Neutrophil" J. of Leukocyte Biology (2004); vol. 75; pp. 25-29.
Rigas, B., et al., "The novel phenylester anticancer compounds: Study of a derivative of aspirin (phoshoaspirin)" International J. of Oncology (2008); vol. 32; pp. 97-100.

(Continued)

*Primary Examiner* — Marcela M Cordero Garcia
(74) *Attorney, Agent, or Firm* — Kenyon & Kenyon LLP

(57) ABSTRACT

The present invention provides a method for inhibiting NF-κB activity in a subject, the method comprising providing an agent capable of inducing expression of annexin 1, whereby said agent induces expression of annexin 1 and whereby said induced expression of annexin 1 inhibits NF-κB activity. Also provided are annexin 1 mimetics capable of binding to NF-κB and pharmaceutical compositions of such inducing and mimetic agents.

56 Claims, 14 Drawing Sheets

(56) References Cited

OTHER PUBLICATIONS

Rigas, B., et al., "Nitric-Oxide-Donating NSAIDs As Agents for Cancer Prevention" TRENDS in Molecular Medicine (2004); vol. 10:7; pp. 324-330.

Scannell, M., et al., "Annexin-1 and Peptide Derivatives Are Released by Apoptotic Cells and Stimulate Phagocytosis to Apoptotic Neutrophils by Marophages", The Journal of Immunology (2007); vol. 178; pp. 4595-4605.

Schimmer, B. P. et al., In Goodman & Gillman's The Pharmacological Basis of Therapeutics, McGraw-Hill 10th ed. (2001); Ch. 60, pp. 1649-1677.

Schumacher, et al., "Identification of D-Peptide Ligans Through Mirror-Image Phage Display", Science (1996); vol. 271; pp. 1854-1857.

Simon, R.J. et al., "Peptoids: A modular approach to drug discovery", Proc. Natl. Acad. Sci. USA (1992); vol. 89; pp. 9367-9371.

Takimoto, E., et al., "Role of Oxidative Stress in Cardiac Hypertrophy and Remodeling" Hypertension (2007); vol. 49; pp. 241-248.

Williams, J. L., et al., "Growth Inhibition of Human Colon Cancer Cells by Nitric Oxide (NO)-Donating Aspirin Is Associated With Cyclooxygenase-2 Induction and B-Catenin/T-Cell Factor Signaling, Nuclear Factor-κB, and NO Synthase 2 Inhibition: Implications for Chemoprevention" Can. Res. (2003); vol. 63; pp. 7613-7618.

Zhang, Z. et al., "NF-κB, Inflammation and Pancreatic Carcinogenesis: NF-κB As a Chemoprevention Target (Review)"; Intl. J. Onc. (2006); vol. 29; pp. 185-192.

Zuckermann, R.N. et al., "Discovery of Nanomolar Ligands for 7-transmembrane G-Protein-Coupled Receptors from Diverse N-(Substitued) glycine Peptoid Library", J. Med Chem. (1994); vol. 37; pp. 2678-2685.

Jacob, C. et al., "Aspects of the biological redox chemistry of cysteine: from simple redox responses to sophisticated signalling pathways", Biol. Chem. (2006); vol. 387; pp. 1385-1397.

* cited by examiner

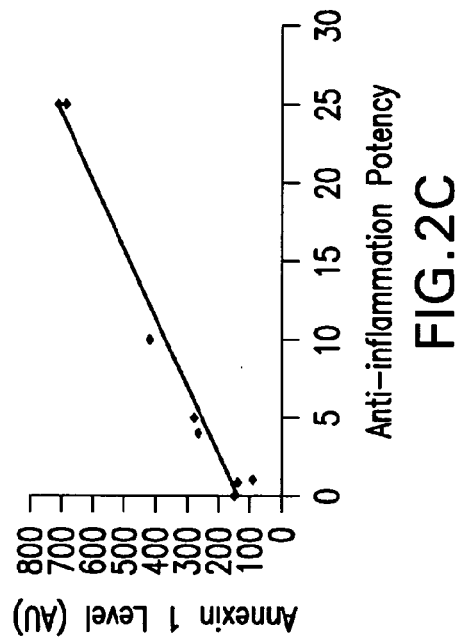
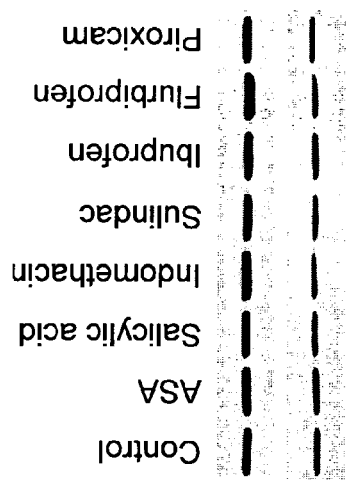
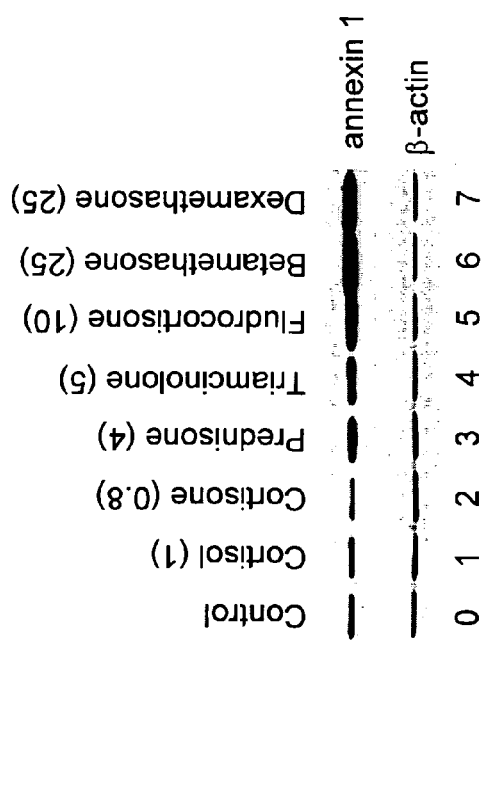
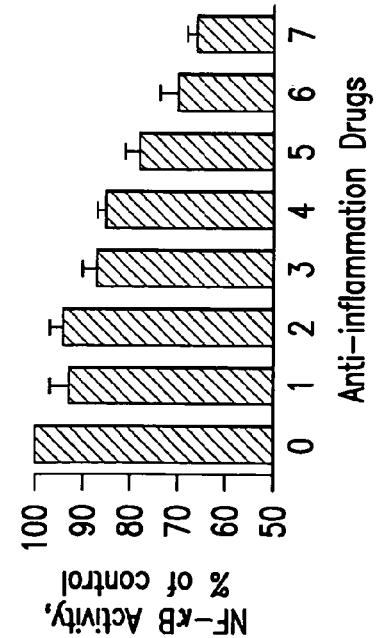
FIG.2A
FIG.2B
FIG.2C
FIG.2D

1: Ac-Gln-Ala-Trp (QW3)
2: Ac-Phe-Gln-Ala-Trp
3: Ac-Phe-Leu-Lys-Gln-Ala-Trp
4: Ac-Phe-Leu-Lys
5: Ac-Lys-Gln-Ala-Trp
6: Ac-Val-Ser-Glu-Lys-Gln-Ala-Trp

INHIBITORS OF NF-κB ACTIVITY

CROSS REFERENCE TO RELATED APPLICATIONS

This application claims priority to U.S. Application No. 60/907,314, filed Mar. 28, 2007, which is incorporated herein by reference in its entirety.

This invention was made with government support under grant number CA101019 awarded by the National Institute of Health. The government has certain rights in the invention.

SEQUENCE LISTING

The instant application contains a Sequence Listing which has been submitted via EFS-Web and is hereby incorporated by reference in its entirety. Said ASCII copy, created on Sep. 9, 2013, is named SUNY-7919-46102-2_ST25.txt and is 12, bytes in size.

BACKGROUND OF THE INVENTION

Nuclear factor-κB (NF-κB), a transcription factor critical to immune responses, is being recognized as an important signaling molecule in the pathogenesis of cancer, underscoring the plausible linkage between inflammation and carcinogenesis (M. Karin, Nature 441:431-436 (2006) and Z. Zhang, B. Rigas, Int. J. Oncol. 29:185-192 (2006)). NF-κB also plays a role in autoimmune responses, cell proliferation and apoptosis by regulating the expression of genes involved in these processes. The activity of NF-κB is tightly regulated by its interaction with inhibitor IκB proteins. In most resting cells, NF-κB (which is usually a heterodimer of p65/RelA and p50) is sequestered in the cytoplasm in an inactive form associated with inhibitory molecules such as IκBα, IκBβ, IκBγ, IκBε, p105 and p100. This interaction blocks the ability of NF-κB to bind to the κB binding site on DNA and thus to modulate gene expression. Following exposure to inflammatory cytokines, UV light, reactive oxygen species, bacteria or viral toxins, the NF-κB signaling cascade is activated, leading to the complete degradation of IκB. This allows for the translocation of unmasked NF-κB to the nucleus where it binds to the enhancer or promoter regions of target genes and regulates their transcription (K. J. Campbell, N. D. Perkins, Biochem. Soc. Symp. 73:165-180 (2006)).

The activation of NF-κB by extracellular inducers depends on the phosphorylation and subsequent degradation of IκB proteins. Activation of NF-κB is achieved through the action of a family of serine/threonine K kinases (IKK). The IKK contains two catalytic subunits (IKKα and IKKβ) and a regulatory/adapter protein NEMO (also known as IKKγ). IKKα and IKKβ phosphorylate IκB proteins and the members of the NF-κB family. All IκB proteins contain two conserved serine residues within their N-terminal area, which are phosphorylated by IKK. IKKα and IKKβ share about 50% sequence homology and can interchangeably phosphorylate Ser$^{32/36}$ of IκBα, and Ser$^{19/23}$ of IκBβ. These phosphorylation events lead to the immediate polyubiquitination of IκB proteins and rapid degradation by the 26S proteasome.

In the nucleus, acetylation of NF-κB determines its active or inactive state. Acetyltransferases play a major role in the acetylation of RelA/p65, principally targeting Lys 218, 221, 310 for modification. Acetylated NF-κB is active and is resistant to the inhibitory effects of IκB. However, when histone deacetylase 3 (HDAC3) deacetylates NF-κB, IκB readily binds to NF-κB and causes its translocation into the cytoplasm. Here HDAC3 serves as an intranuclear molecular switch that turns off the biological processes triggered by NF-κB. One of the target genes activated by NF-κB is that which encodes IκBα. Newly synthesized IκBα in the nucleus removes NF-κB from DNA, and exports the complex back to the cytoplasm to restore its original latent state.

The Rel/NF-κB signal transduction pathway is misregulated in a variety of human cancers, especially those of lymphoid cell origin. Several human lymphomas are reported to have mutations or amplifications of genes encoding NF-κB transcription factors. In most cancer cells NF-κB is constitutively active and resides in the nucleus. In some cases, this may be due to chronic stimulation of the IKK pathway, while in others the gene encoding IκBα may be defective. Such continuous nuclear NF-κB activity not only protects cancer cells from apoptotic cell death, but may even enhance their proliferation. Thus there remains a need for anti-tumor agents that block NF-κB activity or increase the sensitivity of tumors to conventional chemotherapy. There also remains a need for agents to block NF-κB activity to treat or prevent chronic inflammation or autoimmune disorders. The invention presented herein fulfills this need.

SUMMARY OF THE INVENTION

The invention described herein provides a method for inhibiting NF-κB activity in a subject or a cell, the method providing an agent capable of inducing expression of annexin 1, such that the agent induces expression of annexin 1 and this induced expression of annexin 1 inhibits NF-κB activity. In certain embodiments, the agent may be a nitric oxide-donating non-steroidal anti-inflammatory compound such as, but not limited to nitric oxide-donating aspirin (NO-ASA, being any of its positional isomers, i.e. o-, m- or p-). In certain embodiments, the agent may be a phenylester with anticancer and/or anti-inflammatory activities. In certain embodiments, the agent may be an anti-inflammatory compound, such as a corticosteroid, a glucocorticosteroid, or dexamethasone (Dex). In certain embodiments, the agent may be an agent or condition that induces redox changes, including oxidative stress in a target cell or in the subject, which induces expression of annexin 1. In certain embodiments of the invention, annexin 1 (or annexin 1 peptide, variants or homologues) may also be provided to the subject in addition to the aforementioned agents.

The present invention also provides a method for inhibiting NF-κB activity in a subject, by providing annexin 1 or an annexin 1 mimic to the subject. The annexin 1 inhibits NF-κB activity.

In certain embodiments providing annexin 1 in a subject means providing an expression vector comprising a nucleic acid encoding annexin 1 or a fragment thereof, such expression vector capable of expressing annexin 1 or fragment thereof in the subject. In other embodiments, inhibiting NF-κB activity in a subject means providing a peptide derived from annexin 1, whereby said peptide inhibits NF-κB activity. Preferred peptides include Ac-Gln-Ala-Trp (QW-3; SEQ ID NO:1), Ac-Phe-Gln-Ala-Trp (SEQ ID NO:2), Ac-Phe-Leu-Lys-Gln-Ala-Trp (SEQ. ID NO:3), Gln-Ala-Trp (SEQ ID NO:4), Phe-Gln-Ala-Trp (SEQ ID NO:5), Phe-Leu-Lys-Gln-Ala-Trp (SEQ ID NO:6), annexin 1 (SEQ ID NO:8), Ac-Ala-Met-Val-Ser-Glu-Phe-Lys-Gln-Ala-Trp-Phe-Ile-Glu-Asn-Glu-Glu-Gln-Gln-Tyr-Val-Gln-Thr-Val-Lys (SEQ ID NO:10), Ala-Met-Val-Ser-Glu-Phe-Lys-Gln-Ala-Trp-Phe-Ile-Glu-Asn-Glu-Glu-Gln-Gln-Tyr-Val-Gln-Thr-Val-Lys (SEQ ID NO:11), Ac-Ala-Met-Val-Ser-Glu-Phe-Leu-Lys-Gln-Ala-Trp (SEQ ID NO:12), and Ala-Met-Val-Ser-Glu-Phe-Leu-Lys-Gln-Ala-Trp (SEQ ID NO:13), or other peptide fragments of annexin 1, annexin 1, which inhibit NF-κB activity. In certain embodiments, providing a peptide comprises providing an expression vector comprising a nucleic acid encoding the peptide.

In another embodiment of the present invention, a method is provided for inhibiting NF-κB activity in a cell by providing a mimetic of annexin 1, whereby the mimetic inhibits NF-κB activity by physically associating with the NF-κB dimer and preventing binding of the dimer to the NF-κB DNA binding site or making NF-κB ineffective by another mechanism in terms of inducing changes in gene transcription. The inhibitors can be peptides or small molecules. Such mimetics of annexin 1 can be identified by routine screening methods, or can also be predicted, for example, from studies of the 3-dimensional arrangements of annexin 1 bound to NF-κB. Furthermore, the interaction between annexin 1 and NF-κB recognized by the inventors can lead, among other things, to the design of new molecules that inhibit the activity of NF-κB. The design of such molecules is derived from the knowledge of the structural constraints of the binding of NF-κB to annexin 1 as described herein. One of skill in the art will recognize that routine screening of candidate molecules enables the artisan to determine which modeled molecules will inhibit NF-κB by this mechanism.

The present invention also provides pharmaceutical compositions for inhibiting NF-κB activity. These compositions include a therapeutically effective amount of annexin 1, an expression vector comprising a nucleic acid encoding annexin 1, a peptide derived from annexin 1, an expression vector comprising a nucleic acid encoding a peptide derived from annexin 1, or an annexin 1 mimetic such as those synthetic peptides of annexin 1 described above and shown in FIG. 9A, as well as homologues and variants thereof which inhibit NF-κB activity, but not limited to these examples. The pharmaceutical composition may further comprise a nitric oxide-donating non-steroidal anti-inflammatory compound and/or an anti-inflammatory agent and/or phenylester with anticancer or anti-inflammatory activities.

The present invention also provides a method for inhibiting cancer cell growth by providing pharmaceutical compositions of the invention to a subject or a cell, wherein the composition inhibits NF-κB activity and thereby inhibits cancer cell growth.

Another embodiment of the invention also provides a method for inhibiting inflammation by providing the pharmaceutical compositions of the invention to a subject or a cell, wherein the composition inhibits NF-κB activity and thereby inhibits inflammation.

In a further embodiment, the NF-κB inhibitors of this invention are effective in subjects resistant to treatment with steroids. Said inhibitors may be administered as a steroid substitute, or in combination with lower doses of steroids to reduce side effects in subjects in need of such anti-inflammatory treatment.

BRIEF DESCRIPTION OF THE DRAWINGS

FIG. 1 shows the induction of annexin 1 by anti-inflammatory agents such as NO-ASA and Dex in human cancer cell lines.

FIG. 2 shows the induction of annexin 1 and the inhibition of NF-κB activity by corticosteroid anti-inflammatory agents.

FIG. 3 shows the induction of annexin 1 and the promotion of apoptosis and cancer cell death by anti-inflammatory agents.

FIG. 6 shows by confocal microscopy the localization of annexin 1 and NF-κB p65 in NO-ASA or Dex-treated human cancer cells.

FIG. 10 shows that QW-3 (SEQ ID NO:1) inhibits tumor growth, cell proliferation, and inflammation through the inhibition of NF-κB activity in vivo.

DETAILED DESCRIPTION OF THE INVENTION

It has recently been demonstrated that nitric oxide-donating aspirin (NO-ASA) almost completely prevents pancreatic cancer in an animal tumor model (N. Ouyang et al., Cancer Res. 66:4503-4311 (2006)). The mechanism of inhibition of NF-κB by NO-ASA appeared to be important for this effect. NO-ASA, the best-studied member of the novel NO-donating nonsteroidal anti-inflammatory drugs (NO-NSAIDs), shows great promise for the control of cancer. NO-NSAIDs consist of a conventional NSAID to which a NO-donating moiety is linked covalently through a spacer molecule (FIG. 3B) (reviewed in B. Rigas, K. Kashfi, Trends Mol. Med. 10:324-330 (2004)). The distinguishing pharmacological properties of NO-NSAIDs are enhanced potency and greater safety compared to the parent compounds. NO-ASA retains the anti-inflammatory properties of ASA and has strong anticancer effects in preclinical models of cancer.

NO-ASA inhibits NF-κB activity in various cancer cell lines, including pancreatic, colon, and breast. During the study of the mechanism of this effect in human pancreatic and colon cancer cell lines, we noted that NO-ASA induces the expression of annexin 1, an endogenous anti-inflammatory protein (M. J. Hayes, S. E. Moss, Biochem. Biophys. Res. Commun. 322:1166-1170 (2004); V. Gerke, et al., Nat. Rev. Mol. Cell. Biol. 6:449-461 (2005); A. M. Kamal, et al., Mem. Inst. Oswaldo Cruz 100(Suppl 1):39-48 (2005); M. Perretti, R. J. Flower, J. Leukoc. Biol. 76:25-29 (2004)).

The annexins are a family of closely related calcium- and membrane-binding proteins expressed in most eukaryotic cell types. Their diverse functions include vesicle trafficking, cell division, apoptosis, calcium signaling, and growth regulation. Annexins are linked to some of the most serious human diseases such as cardiovascular disease and cancer. Annexin 1, a 37 kDa protein, originally termed lipocortin, inhibits the inflammatory response and participates in several cellular functions, including phagocytosis, extravasation, mediator generation and neutrophil recruitment. In addition, annexin 1 can affect cells relevant to the inflammatory process, such as endothelial, epithelial, mast and synovial cells.

Figures 1A, 1B:
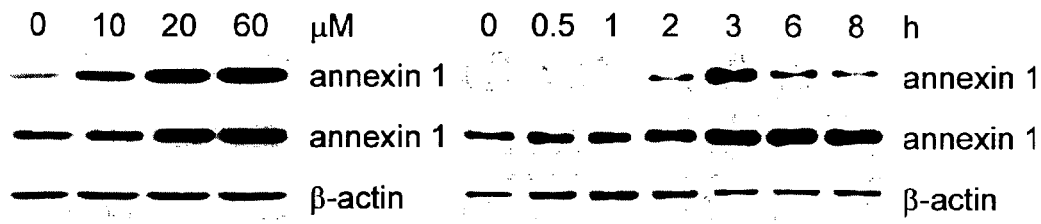
FIGS. 1A and B are Western blots of nuclear and cytoplasmic extracts of annexin 1 after treatment of BxPc-3 cells with NO-ASA.
Figures 1C, 1D:
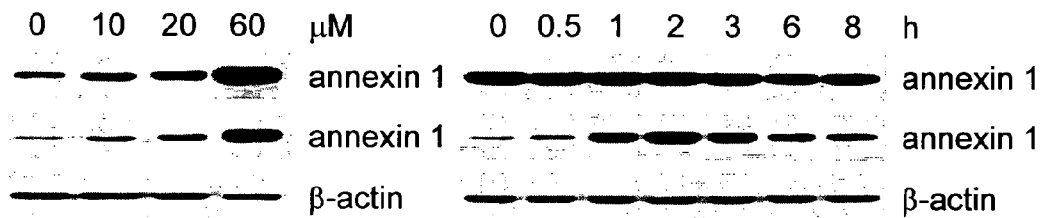
FIGS. 1C and D are Western blots of nuclear and cytoplasmic extracts of annexin 1 after treatment of HT-29 cells with NO-ASA.
Figures 1E, 1F:
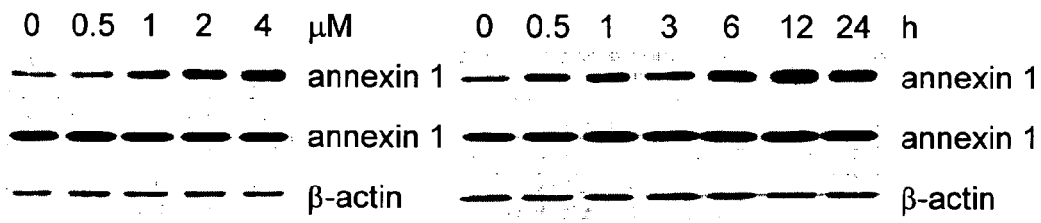
FIGS. 1E and F are Western blots of nuclear (top panel) and cytoplasmic (middle panel) extracts of annexin 1 after treatment of BxPC-3 cells with Dex.
Figures 1H, 1I:
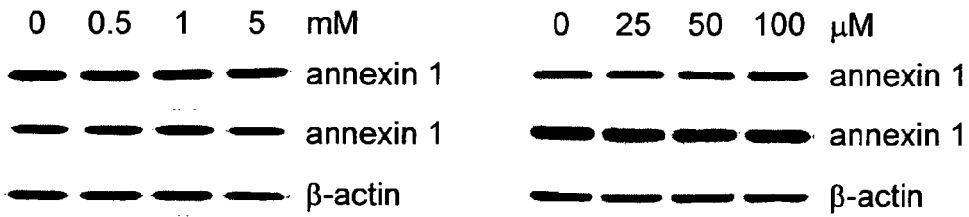
FIGS. 1H and I are Western blots of nuclear and cytoplasmic extracts of annexin 1 from BxPC-3 cells treated with conventional aspirin (ASA) and cortisone.

Using cultured cancer cells and animal tumor models of cancer, the inhibition of NF-κB activity by NO-ASA mediated by annexin 1 was explored. NO-ASA, which inhibits the growth of BxPC-3 human pancreatic cancer cells (FIG. 3B), induced the expression annexin 1 in concentration- and time-dependent manners in human pancreatic cancer BxPC-3 cells (FIGS. 1A and B). The levels of annexin 1 were increased in both the cytoplasm and the nucleus of the cell. In the cytoplasm (FIG. 1B, middle panel) the induction of annexin 1 was rapid, and its levels appeared maximal at 3 h and remained relatively stable for at least 8 h. In the nucleus (FIG. 1B, top panel), the levels of annexin 1 became apparent only at 2 h, peaked sharply at 3 h and declined rapidly thereafter, indicating a time-dependent transport process. The same effect was observed in HT-29 human colon cancer cells (FIGS. 1C and D). Dex, a synthetic corticosteroid with the highest anti-inflammatory potency amongst this class of compounds (B. P. Schimmer, K. L. Parker, Chap. 60 in Goodman & Gillman's The pharmacological basis of therapeutics, J. G. Hardman, L. E. Limbird, Eds. (McGraw Hill, New York, 2001) pp. 1649-1677)) also induced annexin 1 in BxPC-3 cells (FIGS. 1E and F); annexin 1 levels increased progressively over the 24 h of observation. In contrast to NO-ASA and Dex, 5 mM conventional ASA, and 100 μM cortisone, a corticosteroid with weak anti-inflammatory activity, failed to induce the expression of annexin 1 (FIGS. 1H and I). Both were used at concentrations far exceeding those of NO-ASA or Dex that induced annexin 1.

The effect of a variety of natural and synthetic steroids as well as NSAIDs on annexin 1 expression by BxPC-3 cells was also studied. As shown in FIG. 2C, there is a remarkable correlation between the degree of annexin 1 induction and the anti-inflammatory potency of each of the glucocorticoids tested. Interestingly, the induction of annexin 1 was accompanied by suppressed NF-κB activity (FIGS. 2A and B). In contrast, none of the NSAIDs tested induced annexin 1 (FIG. 2D); they represent the following structural groups of this large family of compounds: salicylic acid derivatives (for example, ASA and salicylic acid); indole and indene acetic acids (for example, indomethacin and sulindac); arylpropionic acids (for example, ibuprofen and flurbiprofen); and enolic acids (for example, piroxicam).

Figure 3A:
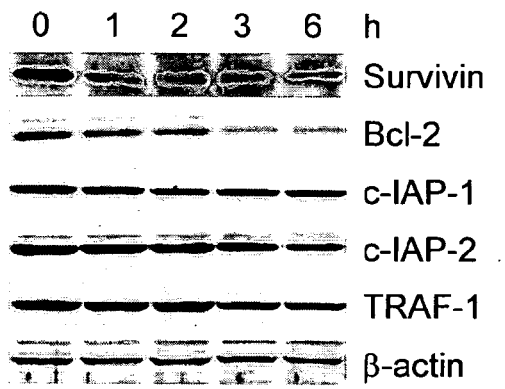
FIG. 3A is a Western blot that shows the effect of NO-ASA treatments of BxPC-3 cells on NF-κB dependent gene products survivin, Bcl-2, c-IAP, c-IAP-2 and TRAF-1.
Figure 3B:
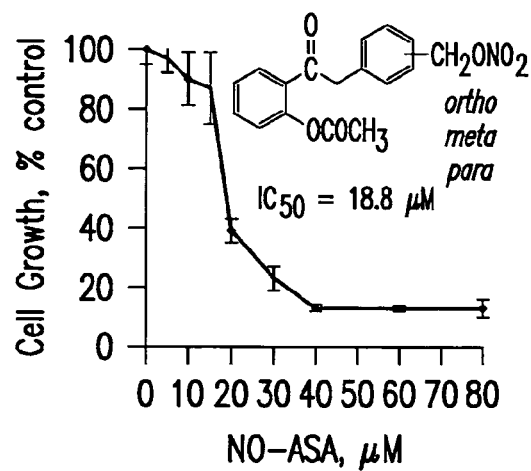
FIG. 3B shows the effect of BxPC-3 cell growth by NO-ASA measured by a MTT assay.
Figure 3C:
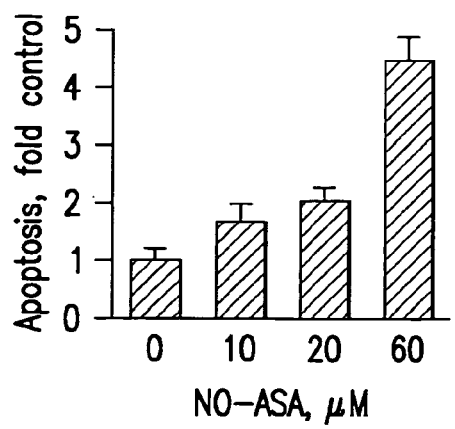
FIG. 3C shows the effect of annexin 1 on apoptosis promoted by NO-ASA.
Figure 3D:
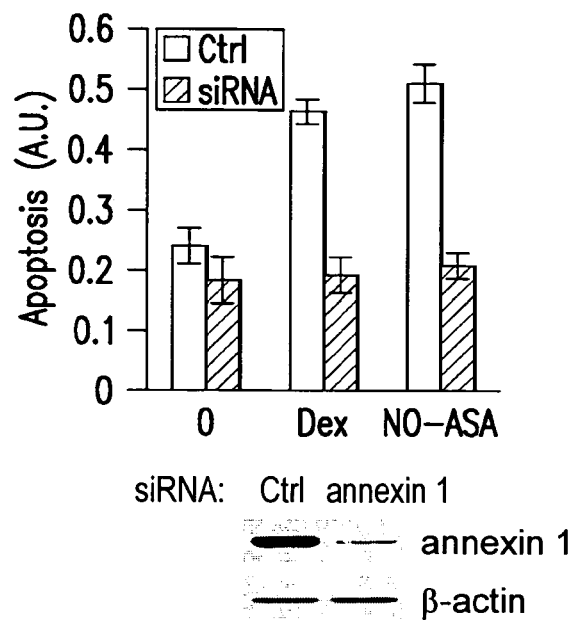
FIG. 3D shows the effect of knock-down expression of annexin 1 on HT-29 cell apoptosis induced by either Dex or NO-ASA.
Figure 3E:
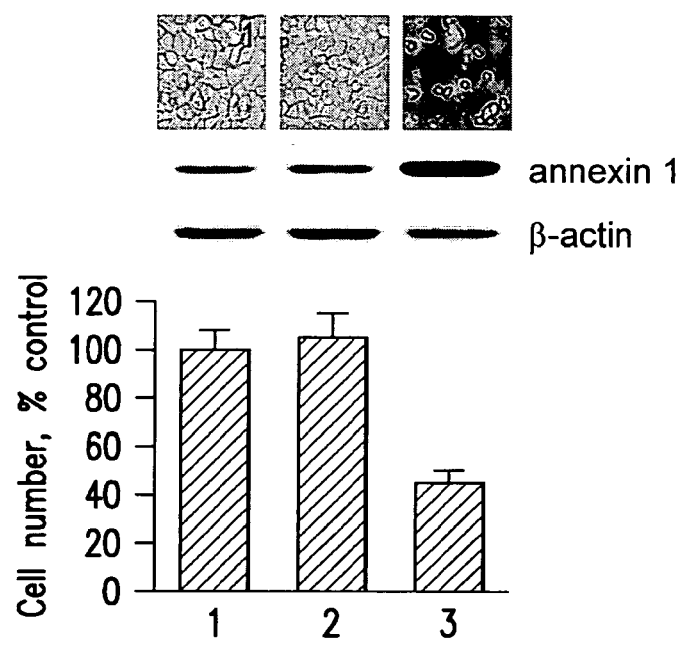
FIG. 3E shows that overexpression of annexin 1 by transferring its cDNA into BxPC-3 cells resulted in cell death through inhibition of NF-κB activity.

The effect of NO-ASA on annexin 1 expression was paralleled by promotion of human cancer cell apoptosis and cell death. The expression of Bcl-2, an NF-κB dependent gene, which suppresses apoptosis, was inhibited by NO-ASA in BxPC-3 cells, as were the apoptosis-related proteins survivin, Bcl-2, c-IAP-1, c-IAP-2 and TRAF-1 (FIG. 3A). Inhibition of HT-29 cell growth (IC$_{50}$=18.8 μM at 24 h) (FIG. 3B), by NO-ASA was predominantly through apoptosis (FIG. 3C). The induction of apoptosis was paralleled by the induction of annexin 1 (FIG. 1C). Knocking-down the expression of annexin 1 using its specific siRNA completely abrogates the cell apoptosis induced by NO-ASA (FIG. 3D), indicating that annexin 1 is a key player in NO-ASA mediated apoptosis. Interestingly, forced expression of annexin 1 by transfecting an annexin 1 cDNA construct into BxPC-3 cells increases cell death through the inhibition of NF-κB activity by about 45%. A control plasmid failed to have such an effect (FIG. 3E).

Overexpression of annexin 1 by transfection of an annexin 1 DNA construct into BxPC-3 cells increased cell death through the inhibition of NF-κB activity by about 45%. A control plasmid failed to have such an effect (FIG. 3E).

To clarify the effect of the induction of annexin 1 on cell apoptosis through inhibition of NF-κB, BxPC-3 or HT-29 cells were exposed to either NO-ASA or Dex for 3 h. NF-κB activity was measured in the cells using an ELISA assay. NO-ASA or Dex inhibited NF-κB activity in a concentration-dependent manner in both HT-29 (FIGS. 4A and C) and BxPC-3 (FIGS. 4B and D) cells.

To further examine the inhibitory effect of annexin 1 on NF-κB activity, the expression of annexin 1 in BxPC-3 cells was knocked down using annexin 1-specific siRNA. While NO-ASA 20 μM suppressed NF-κB activity by 40% in the treated BxPC-3 cells, when the expression of annexin 1 was greatly reduced by siRNA, NO-ASA had only a marginal effect (10% reduction) on NF-κB activity (FIG. 4E). Interestingly, compared to control (nonspecific siRNA), NF-κB activity was enhanced by siRNA against annexin 1, suggesting that annexin 1 exerts a baseline inhibitory effect on NF-κB activity.

Figure 5A:
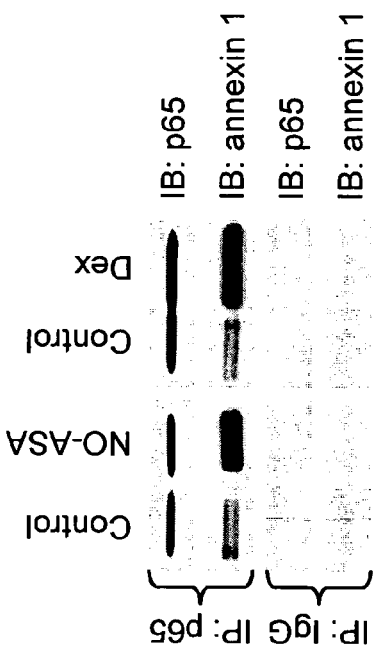
FIG. 5A shows that the induced annexin 1 and NF-κB bound to the κB-recognition site on double-stranded DNA oligomers.
Figure 5B:
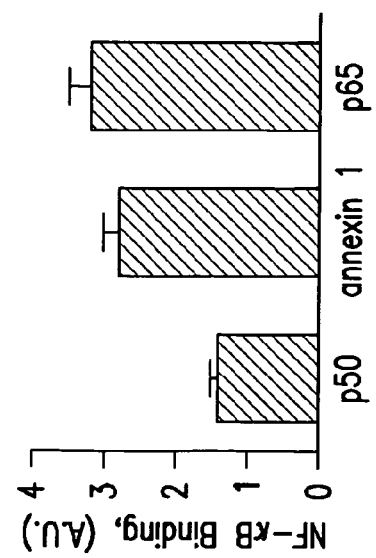
FIGS. 5B and C show the immunoblots of anti-p65 (NF-κB) precipitated nuclear extract protein from BxPC-3 cells and HT-29 cells treated either with NO-ASA or Dex.
Figure 5C:
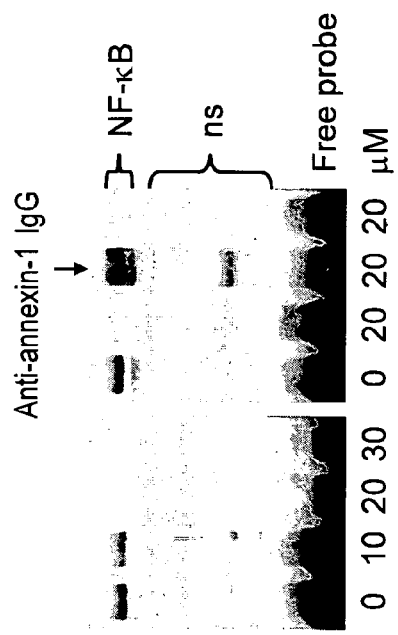
FIG. 5 shows that annexin 1 physically bound to NF-κB p65 from nuclear extracts of human cancer cells treated with either NO-ASA or Dex.
FIG. 5D shows by electrophoretic mobility shift assay (EMSA) that annexin 1 interferes with the binding of NF-κB to the double-stranded κB probe.
Figure 5D:
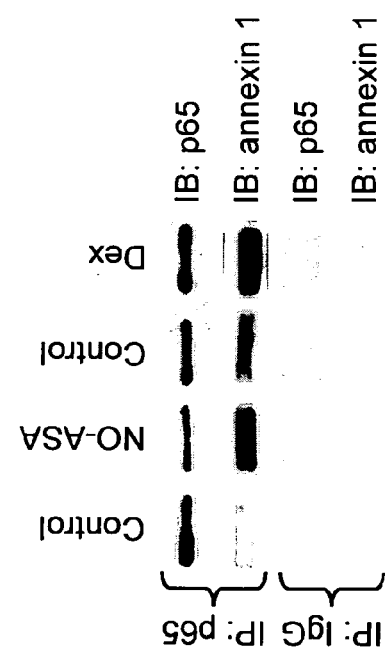

It was then demonstrated that annexin 1 is physically associated with the NF-κB dimer. First, nuclear extract from BxPC-3 cells treated for 3 h with or without NO-ASA 20 µM was reacted with immobilized double-stranded oligomers 5'-CATCGGAAATTTCCGGAAATTTCCG-GAAATTTCCGGC-3' and its complement) (SEQ ID NO:9) that contained the NF-κB recognition sequence, in the reaction well. The NF-κB dimers bound to the κB oligomers were recognized by anti-p65 or anti-p50 antibodies through a color reaction dependent upon a secondary antibody in an ELISA assay. When an anti-annexin 1 mAb that did not cross-react with either p50 or p65 was used instead of the anti-p65 or anti-p50 antibodies, a positive reaction (recognition of the protein bound to the κB oligomers) was obtained (FIG. 5A); a nonspecific isotypic antibody gave a negative result. These results suggested that either annexin 1 was associated with the NF-κB dimer or it cross-bound to the κB oligomers. To differentiate between these alternatives, the nuclear proteins from BxPC-3 or HT-29 cells treated with NO-ASA 20 µM or Dex 4 µM for 3 h were immunoprecipitated with an anti-p65 mAb. The immunoprecipitates were electrophoresed in SDS-PAGE and subsequently immunoblotted with the anti-annexin 1 mAb revealing the presence of markedly increased amounts of annexin 1 in the NO-ASA or Dex-treated cells compared to controls (FIG. 5B for BxPC-3 and 5C for HT-29 cells). Immunoprecipitation with an isotypic non-specific mAb failed to precipitate annexin 1. Finally, an EMSA was performed using nuclear extracts from BxPC-3 cells treated with NO-ASA. Increasing concentrations of NO-ASA markedly suppressed the binding of NF-κB to the κB probe (SEQ ID NO:9) (FIG. 5D, left panel), as had been found in HT-29 cells (J. L. Williams et al., Cancer Res. 63:7613-7618 (2003)). However, when the nuclear extract from NO-ASA treated cells was pre-incubated with anti-annexin 1 mAb before the nuclear protein κB probe binding step (taking the annexin 1 out of the complex formation), the binding of p50/p65 to the κB oligomer was restored, as evidenced by a strong band in the EMSA. A nonspecific control antibody had no such effect (FIG. 5D, right panel). This finding suggests that annexin 1 bound to the NF-κB dimer and prevents its binding to the DNA κB binding site.

Confocal microscopy studies further support the inventors' findings that NO-ASA and Dex induce the expression of annexin 1 and that annexin 1 associates physically with the NF-κB dimer. BxPC-3 cells reacted with mAbs to p65 and annexin 1 were examined for colocalization of these two proteins. In untreated cells, the two proteins colocalized minimally if at all. In response to a 2 h treatment with NO-ASA, there was marked concentration-dependent colocalization of p65 and annexin 1. At NO-ASA 20 µM, colocalization was more pronounced in the nuclei (FIG. 6A), consistent with the enhanced nuclear annexin 1 levels detected by immunoblotting (FIGS. 1A and B). Dex generated similar results (FIG. 6B).

Figure 7A:
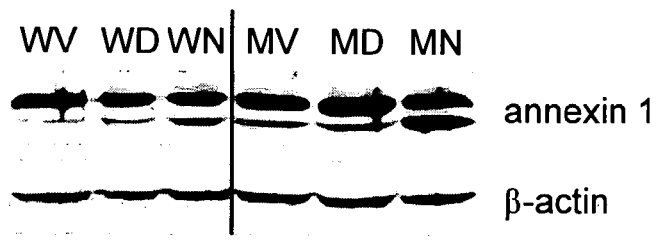
FIG. 7 shows the induction of annexin 1 and inhibition of NF-κB by NO-ASA or Dex in an animal model of cancer. The Western blot in FIG. 7A shows the induction of annexin 1 by NO-ASA or Dex in wild-type and Min mice.
FIG. 7B shows the inhibition of NF-κB activity by NO-ASA or Dex in wild-type and Min mice as measured by an ELISA assay.
FIG. 7C is the immunoblots of anti-p65 (NF-κB) precipitated nuclear extract protein from the epithelial cells from mice treated either by NO-ASA or Dex. The Western blots in FIGS. 7D and E show the suppression of NF-κB dependent gene Bcl-xL expression from the epithelial cells from wild-type and Min mice treated either NO-ASA or Dex.
Figure 7B:
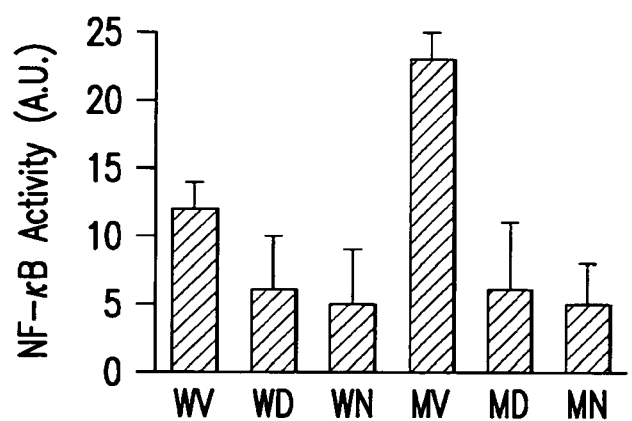
Figure 7C:
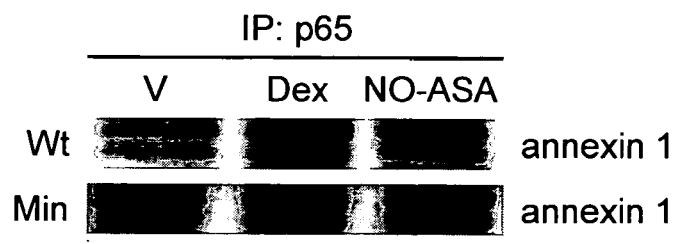
Figure 7D:
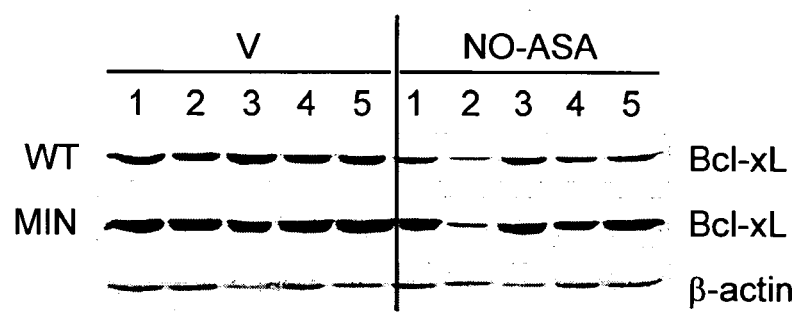
Figure 7E:
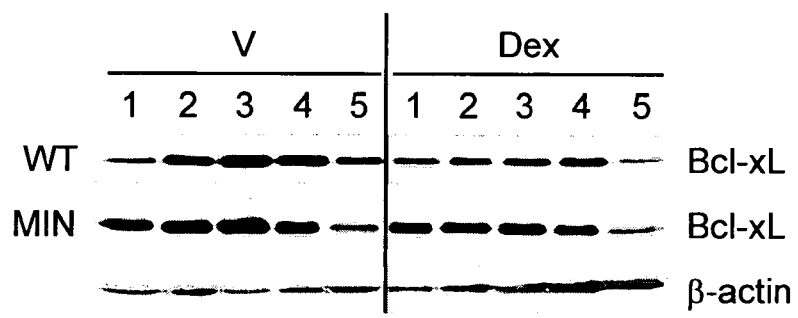
Figure 8A:
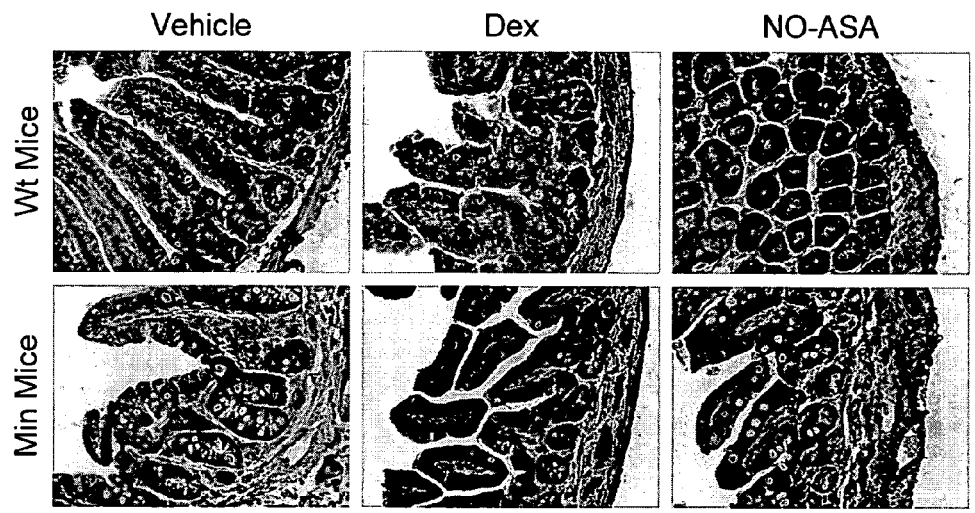
FIG. 8 shows the induction of annexin 1 and inhibition of NF-κB in vivo by immunohistochemistry. The immunohistochemistry images in FIGS. 8A and B show the induction of annexin 1 and inhibition of NF-κB by Dex or NO-ASA in both wild-type and Min mice.
FIG. 8C shows the colocalization of annexin 1 and NF-κB p65 in intestinal epithelial cells from mice treated with NO-ASA.
Figure 8B:
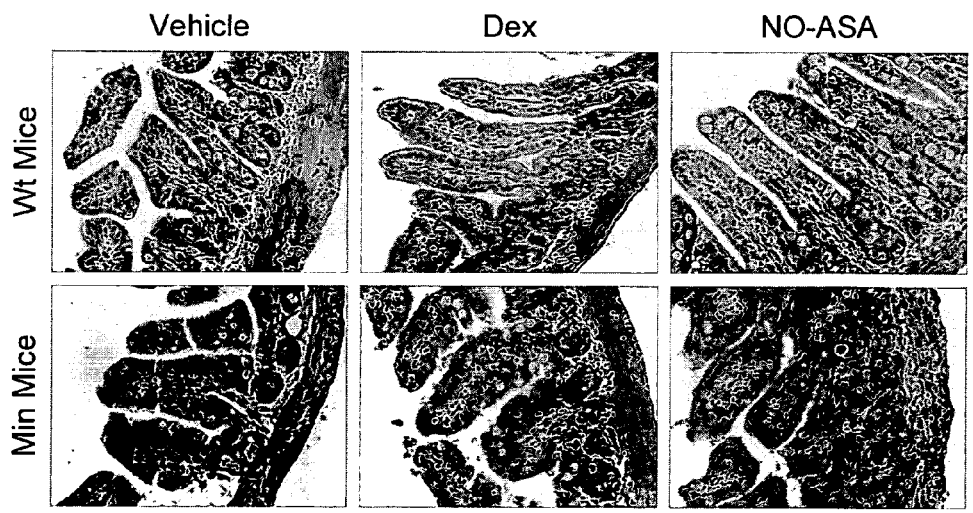
Figure 8C:
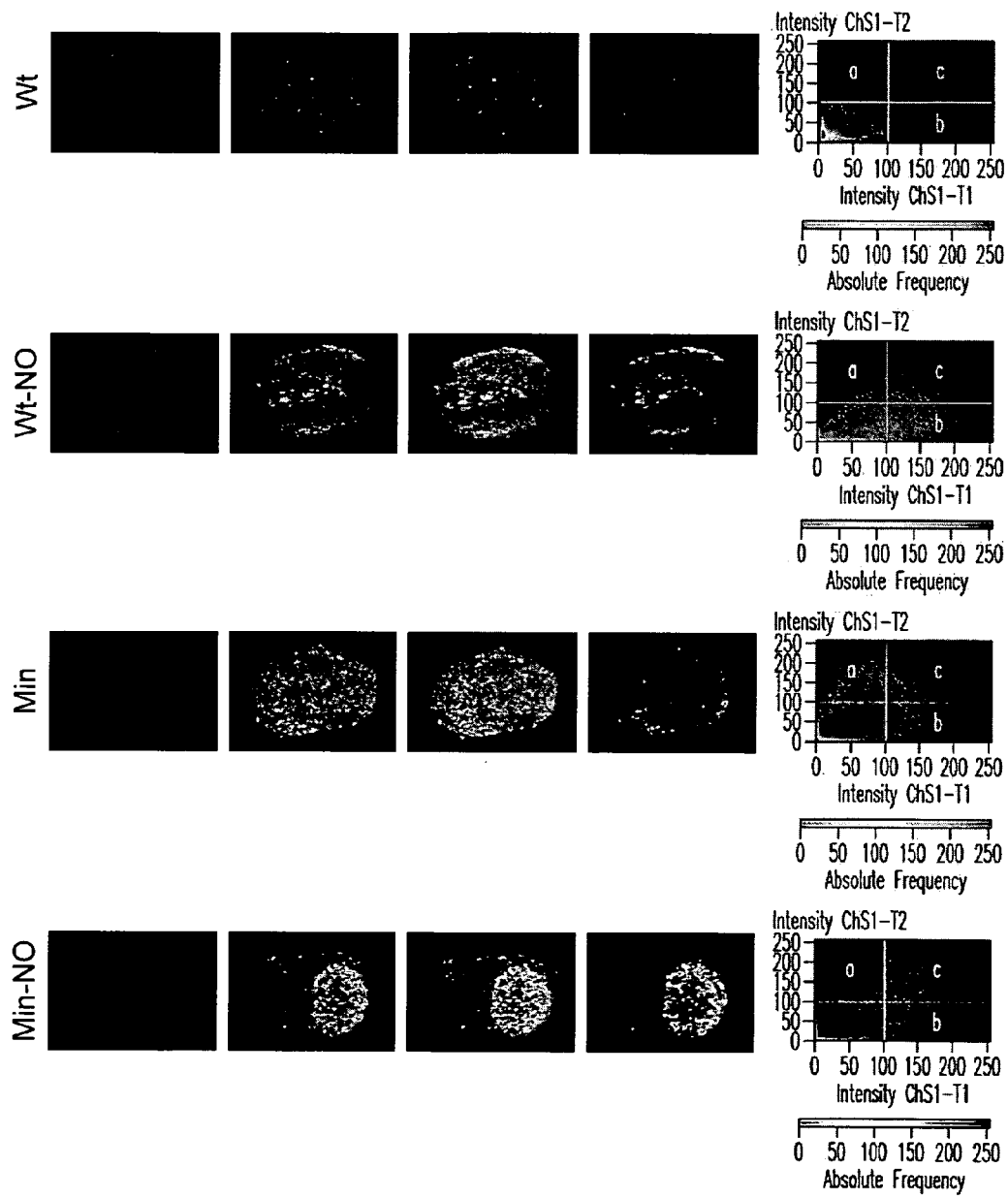

To assess whether these changes occur in vivo, the inventors studied isolated small intestine epithelial cells from Min mice and the corresponding wild type mice C57BL/6J (of which the Min mice are a congenic derivative) treated with NO-ASA 100 mg/kg or Dex 10 mg/kg daily for 7 days. Min (multiple intestinal neoplasia), a mutant allele of the murine APC (adenomatous polyposis coli) locus, encodes a nonsense mutation at codon 850. Heterozygous Min mutants spontaneously develop tumors in the intestine and represent a model of intestinal carcinogenesis (M. Lipkin et al., Ann. N.Y. Acad. Sci. 889:14-19 (1999); A. Moser, H. Pitot, W. Dove, Science 247:322-324 (1990)). The levels of annexin 1 were increased in both Min and wild-type mice treated with either NO-ASA or Dex (FIG. 7A and FIG. 8A). The induction of annexin 1 by NO-ASA or Dex was accompanied by the inhibition of NF-κB activity (FIGS. 7B and 8B). NF-κB activity in NO-ASA or Dex-treated Min mice was significantly inhibited compared to the control group because induced annexin 1 bound physically to NF-κB p65 (FIG. 7C), leading to suppression of its dependent gene expression (FIGS. 7D and E). Intestinal cells from untreated wild type mice showed no detectable colocalization of annexin 1 and p65 (FIG. 8C, Wt panel). Treatment of these mice with NO-ASA led to a modest but significant colocalization of these two proteins, which was mostly cytoplasmic (FIG. 8C, Wt-NO panel). Intestinal cells from untreated Min mice showed limited colocalization of these proteins (FIG. 8C, Min panel), which was greatly enhanced in cells from treated mice, being present almost exclusively in the nucleus (FIG. 8C, Min-NO panel).

Figure 9A:
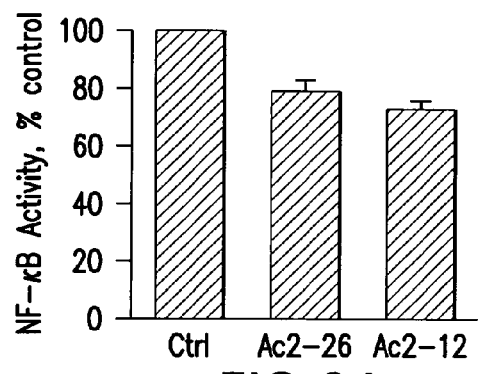
FIG. 9A shows that the commercial peptides of annexin 1 (SEQ ID NO:7), Ac2-26 (SEQ ID NO:10), and Ac2-12 (SEQ ID NO:12) inhibit NF-κB activity in BxPC-3 cells.

Recent studies have emphasized that the N-terminal sequence of annexin 1 can reproduce the anti-inflammatory actions of the full-length protein (Scannell, M. et al., J Immunol 178:4595-605 (2007)). These commercial peptides of annexin 1, Ac2-26 and Ac2-12, (SEQ ID NO:10 and 12) inhibit NF-κB activity in BxPC-3 cells as shown in FIG. 9A. Furthermore, N-terminal peptides of the annexin 1 protein were designed and synthesized by the inventors. These synthetic peptides inhibit NF-κB activity (FIG. 9B) in BxPC-3 cells. QW-3 (SEQ ID NO:1) inhibits NF-κB activity (FIG. 9C) and enhances apoptosis (FIG. 9D) in SW480 human colon cancer cells.

To assess whether these effects occur in vivo, the inventors further investigated the effect of QW-3 on tumor xenografts of nude mice. Xenografts of SW480 human colon cancer cells were established by s.c. injection of cells into the upper portion of the left hind limb of the mice, where they grew as solid tumors. Mice were treated with QW-3 administered by i.p. injections. The control group was administered vehicle alone. The mice were sacrificed on day 12, and tumors were resected and stored in liquid nitrogen and formalin until further analysis.

Figure 10A:
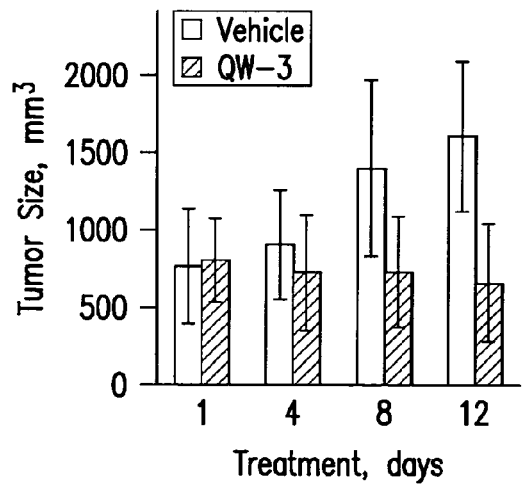
FIG. 10A shows that QW-3 inhibits tumor growth in SW480 tumor xenografts of nude mice.
Figure 10C:
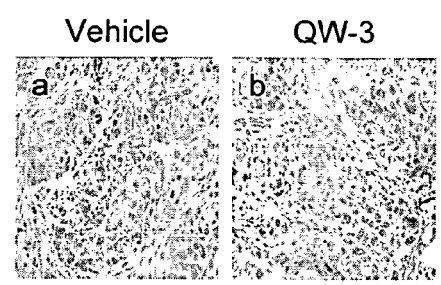
FIG. 10C shows that QW-3 inhibits NF-κB activity.

QW-3 suppressed tumor growth in tumor xenografts. Tumors in the mice treated with QW-3 stopped growing, and regressed (FIG. 10A). This was also demonstrated by immunohistochemistry which shows that QW-3 inhibited cell proliferation by the expression of PCNA, a marker for cell proliferation in nuclei (as evidenced by lack of staining in FIG. 10B). QW-3 also inhibited NF-κB activity (FIG. 10C). QW-3 also increased blood levels of IL-10, an anti-inflammatory cytokine, and decreased those of IL-6 (FIG. 10D), a pro-inflammatory cytokine, indicating that this short peptide of annexin 1 suppresses inflammation.

The data presented herein reveal hitherto unrecognized roles of annexin 1 and its mimetics, which explain many of its reported activities; establish a novel control mechanism of NF-κB activity; and suggests a potential mechanism for the action of anti-inflammatory agents, including some corticosteroids.

An important point is the observation that weak anti-inflammatory drugs such as conventional ASA and cortisone do not induce annexin 1 and do not inhibit the activity of NF-κB. Thus, it is clear that this mechanism mediates preferentially strong anti-inflammatory and strong anticancer effects. In addition, these findings suggest potential targets for drug development such as agents that will enhance or mimic the inhibitory effect of annexin 1 on NF-κB, thus bypassing the considerable side effects of conventional anti-inflammatory agents, including corticosteroids.

Accordingly, the present invention provides a method for inhibiting NF-κB activity in a subject or a cell. A subject includes, but is not limited to, mammals and humans. "Inhibiting NF-κB activity" includes not only complete inhibition but also transient and partial inhibition. It also includes a reduction in NF-κB activity as compared to the level of activity before methods of the present invention were employed.

The method involves providing an agent that is capable of inducing expression of annexin 1 to the subject or cell, in vitro or in vivo. As exemplified herein, inducing expression of annexin 1 by anti-inflammatory agents results in the inhibition of NF-κB activity. It has been shown herein that annexin 1 associates physically with the NF-κB dimer and prevents its binding to the DNA κB binding site, thus reducing NF-κB activity (and hence reducing the ability of NF-κB to initiate expression of various genes related to inflammation, cell renewal and cell death).

The term "prevents binding to the DNA κB binding site" means not only a total prevention of binding but also a partial prevention of binding or a reduced level of binding as compared to binding in situations where methods of the present invention are not employed.

"Inducing expression of annexin 1" means not only turning on expression but also increasing the level of expression as compared to expression levels before the agent was administered. The agent may be any agent or treatment that induces or increases expression of annexin 1. Exemplary agents include nitric oxide-donating non-steroidal anti-inflammatory compounds (NO-NSAIDs) such as, but not limited to, nitric oxide-donating aspirin (NO-ASA). Any other nitric oxide-donating compound, whether it is a non-steroidal anti-inflammatory compound or other agent synthetic or natural may also be used. In a preferred embodiment the agent comprises NO-ASA. Another exemplary group of agents is the novel phenylester compounds, including phosphoaspirin (Rigas B, Kozoni V, Int. J. Oncol. 32:97-100 (2008) that display anti-cancer properties.

In another embodiment of the invention, the agent that is capable of inducing expression of annexin 1 (and results in annexin 1 inhibiting NF-κB activity) is a known anti-inflammatory compound such as, but not limited to, prednisone, triamcinolone, fludrocortisone, betamethasone, or Dex. In certain embodiments the agent comprises Dex.

In certain embodiments of the invention, the agent may be any agent or condition that induces redox changes, including oxidative stress in the target cell, in vitro, or in the target cell of the subject, in vivo. Induction of oxidative stress has been shown to induce expression of annexin 1. Thus, as shown above, induction of annexin 1 inhibits NF-κB activity.

Oxidative stress denotes a persistent (over longer time periods) and often irreversible oxidative shift that characterizes a pathophysiological state. It has been defined as an imbalance between oxidants and antioxidants in favor of the former, resulting in an overall increase in cellular levels of reactive oxygen species. Reactive oxygen species (ROS) and reactive nitrogen species (RNS) are produced by mitochondria ($O_2.^-$, $H_2O_2$, .OH); cytochrome P450 ($O_2.^-$, $H_2O_2$); macrophages ($O_2.^-$, $H_2O_2$, .NO); and peroxisomes ($H_2O_2$). Normal cellular metabolism does generate ROS; in a normal person 10,000-20,000 free radicals attack each body cell each day. Cellular antioxidants include: classic antioxidant enzymes (superoxide dismutase (SOD), catalase, glutathione (GSH) peroxidase, glutaredoxine and thioredoxin); non-classic antioxidant enzymes (e.g., heme oxygenase-1); Phase II detoxifying enzymes (recently shown to be protective, such as GSH reductase, NQO1, and GSH transferase (J. W. Fahey, P. Talalay, Food Chem. Toxicol. 37:973-979 (1999)); and non-enzymatic antioxidants (vitamins E and C, GSH and catechins) Many of the cellular antioxidants are regulated in part by the redox status of the cell.

Conditions that shift this balance in favor of the pro-oxidant agents cause oxidative stress; for example, agents such as DL-buthionine-(S,R)-sulfoximine (BSO), which inhibits GSH biosynthesis (O. W. Griffith, A. Meister, J. Biol. Chem. 254:7558-7560 (1979)) that reduce glutathione levels create oxidative stress.

A free radical is any chemical species capable of independent existence possessing one or more unpaired electrons. Biological free radicals are thus highly unstable molecules that have electrons available to react with various organic substrates. Agents and conditions that induce oxidative stress are known in the art. NO-ASA is one such agent (J. Gao et al, Proc. Natl. Acad. Sci. USA 102:17207-17212 (2005). See e.g., E. Takimoto, D. A. Kass, Hypertension 49:241-248 (2007); B. Halliwell, Biochem. J. 401:1-11 (2007); and C. Jacob et al., Biol. Chem. 387:1385-1397 (2006)).

Another embodiment of the invention provides a method for inhibiting NF-κB activity in a subject or a cell comprising providing annexin 1 to the subject or the cell. By providing annexin 1 to the subject or to the cell, the annexin 1 is available to inhibit NF-κB activity as described above. The annexin 1 can be provided as the annexin 1 protein or as an expression vector comprising a nucleic acid encoding annexin 1. The expression vector is capable of expressing annexin 1 in the subject or the cell Annexin 1 has a molecular weight of about 37 kDa and consists of about 346 amino acids. The amino acid sequence is known by one skilled in the art as Genbank accession number P04083 (SEQ ID NO:8). The nucleic acid sequence encoding annexin 1 is known by one skilled in the art as Genbank accession number NM 000700 (SEQ ID NO:7). Annexin 1 peptides are peptide fragments of annexin 1, and are shorter than annexin 1, but have similar biological affects on a cell Annexin peptides include, but are not limited to Ac-Gln-Ala-Trp (SEQ ID NO:1), the peptide Ac-Phe-Gln-Ala-Trp (SEQ ID NO:2), the peptide Ac-Phe-Leu-Lys-Gln-Ala-Trp (SEQ ID NO:3), the peptide Gln-Ala-Trp (SEQ ID NO:4), the peptide Phe-Gln-Ala-Trp (SEQ ID NO:5), the peptide Phe-Leu-Lys-Gln-Ala-Trp (SEQ ID NO:6), the peptide set forth in SEQ ID NO:8, the peptide set forth in SEQ ID NO:10, the peptide set forth in SEQ ID NO:11, the peptide Ac-Ala-Met-Val-Ser-Glu-Phe-Leu-Lys-Gln-Ala-Trp (SEQ ID NO:12), the peptide Ala-Met-Val-Ser-Glu-Phe-Leu-Lys-Gln-Ala-Trp (SEQ ID NO:13), or other fragments of annexin 1, as long as they maintain the ability to inhibit NF-κB activity.

With respect to homologues of annexin 1, one skilled in the art would understand that a homologue shares sufficient homology with annexin 1 so as to have similar effects on the cell as annexin 1. With respect to variants, one skilled in the art would appreciate that conservative mutations would more likely preserve the ability of the annexin 1 variant or homologue to inhibit NF-κB activity. The skilled artisan will further appreciate that changes can be introduced by mutation into the nucleotide sequence thereby leading to changes in the amino acid sequence of the encoded annexin 1 protein, without altering the functional ability of the annexin 1 protein. The term "functional ability" means that the variant or homologue is able to inhibit NF-κB activity by associating with the NF-κB dimer, thus limiting its ability to bind to the κB binding site on DNA. For example, nucleotide substitutions leading to amino acid substitutions at "non-essential" amino acid residues can be made in the sequence. A "non-essential"

amino acid residue is a residue that can be altered from the wild-type sequence of annexin 1 without altering the biological activity, whereas an "essential" amino acid residue is required for biological activity. Also included are nucleic acid molecules encoding annexin 1 protein that contain changes in amino acid residues that are not essential for activity and as such retain biological activity. Likewise, the invention encompasses homologs and variants of annexin 1 peptides.

The invention provides nucleic acids that encode the annexin 1 polypeptides and homologs. In certain embodiments, the isolated nucleic acid molecule comprises a nucleotide sequence encoding a protein, wherein the protein comprises an amino acid sequence at least about 75% homologous to the wild-type annexin 1. Preferably, the protein encoded by the nucleic acid is at least about 80% homologous, more preferably at least about 90%, 95%, 98%, and most preferably at least about 99% homologous to the wild-type amino acid sequences. An isolated nucleic acid molecule encoding an annexin 1 protein homologous to wild-type annexin 1 of SEQ ID NO:8 can be created by introducing one or more nucleotide substitutions, additions or deletions into the nucleotide sequence, such that one or more amino acid substitutions, additions or deletions are introduced into the encoded protein.

Mutations can be introduced into the annexin 1 nucleotide sequence (e.g., SEQ ID NO:7) by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in annexin 1 is replaced with another amino acid residue from the same side chain family. Alternatively, in another embodiment, mutations can be introduced randomly along all or part of the annexin 1 coding sequence, such as by saturation mutagenesis, and the resultant mutants can be screened for annexin 1 biological activity to identify mutants that retain activity. Following mutagenesis the encoded protein can be expressed by any recombinant technology known in the art and the activity of the protein can be determined. Alternatively, the nucleic acid or protein can be manually synthesized with the desired mutations.

Annexin 1 variants as used herein include biologically active portions of annexin 1, or derivatives or fragments thereof as long as they retain their functional activity as described above. For example, an annexin 1 variant includes a mutant or variant protein any of whose residues may be changed from the corresponding residue in the wild-type sequences while still encoding a protein that maintains its annexin 1-like activities and physiological functions, or a functional fragment thereof. In some embodiments, 20% or more of the residues may be so changed in the mutant or variant protein.

In general, an annexin 1 variant that preserves annexin 1-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention as long as the functional activity is maintained. In favorable circumstances, the substitution is a conservative substitution as defined above.

The peptides of annexin 1 described in Example 10 have biological activity similar to the full length protein in terms of NF-κB inhibition Annexin 1 and the peptides derived from annexin 1 inhibit NF-κB activity by physically associating or interacting with the NF-κB dimer and retain NF-κB inhibitory activity (e.g., inhibit its ability to bind to the κB DNA binding site). Modifications to these peptides, including acetylation and the inclusion of non-physiological amino acids to enhance stability of the peptides can be made. Accordingly, any peptide derived from annexin 1 that inhibits NF-κB activity by physically associating with the NF-κB dimer and inhibits its ability to bind to the κB DNA binding site is contemplated by the present invention. Preferred embodiments include the peptide Ac-Gln-Ala-Trp (SEQ ID NO:1), the peptide Ac-Phe-Gln-Ala-Trp (SEQ ID NO:2), the peptide Ac-Phe-Leu-Lys-Gln-Ala-Trp (SEQ ID NO:3), the peptide Gln-Ala-Trp (SEQ ID NO:4), the peptide Phe-Gln-Ala-Trp (SEQ ID NO:5), the peptide Phe-Leu-Lys-Gln-Ala-Trp (SEQ ID NO:6), the peptide set forth in SEQ ID NO:10, the peptide set forth in SEQ ID NO:11, the peptide Ac-Ala-Met-Val-Ser-Glu-Phe-Leu-Lys-Gln-Ala-Trp (SEQ ID NO:12), the peptide Ala-Met-Val-Ser-Glu-Phe-Leu-Lys-Gln-Ala-Trp (SEQ ID NO:13), or other peptide fragment of annexin 1 as long as they maintain the ability to inhibit NF-κB activity.

In another embodiment of the invention, the peptides derived from annexin 1 are provided to the subject or cell by providing an expression vector comprising a nucleic acid encoding the peptides derived from annexin 1, wherein the expression vector is capable of expressing the peptides. Preferred nucleic acids encode the peptide set forth in SEQ ID NO:4, the peptide set forth in SEQ ID NO:5, the peptide set forth in SEQ ID NO:6, the peptide set forth in SEQ ID NO:10, the peptide set forth in SEQ ID NO:11, the peptide set forth in SEQ ID NO:13, or other peptide fragments of annexin 1, as long as they maintain the ability to inhibit NF-κB activity. One skilled in the art would appreciate and understand suitable expression vectors, promoters, enhancers, etc. to employ to provide transient or stable expression at the desired level in the particular subject or cell.

Annexin 1 mimetics include annexin 1 peptides, homologs, and variants and further include small molecules that mimic the activity of annexin 1 by binding to the annexin 1 binding site of NF-κB and inhibiting NF-κB activity. "Small molecule" refers to compounds that have a molecular weight up to about 2000 atomic mass units (Daltons). Any small molecule can be tested to determine whether it inhibits annexin 1/NF-κB complex formation. In practice, small molecules to be tested are often compounds understood to have biological activity, which may be under development for pharmaceutical use. Generally such compounds will be organic molecules, which are typically from about 100 to 2000 Da, more preferably from about 100 to 1000 Da in molecular weight. Such compounds include peptides and derivatives thereof, steroids, anti-inflammatory drugs, anti-cancer agents, anti-bacterial or antiviral agents, neurological agents and the like. In principle, any compound under development in the field of pharmacy can be used in the present invention in order to facilitate its development or to allow further rational drug design to improve its properties. Libraries of high-purity small organic ligands and peptide agonists that have well-documented pharmacological activities are available from numerous sources, and can be screened directly or used in virtual screens.

Annexin 1 mimetics can also be found among "unnatural biopolymers" such as polymers consisting of chiral aminocarbonate monomers substituted with a variety of side chains. Cho et al, 1998, J. Am. Chem. Soc. discloses libraries of linear and cyclic oligocarbamate libraries and screening for binding to the integrin GPIIb/IIIa. Simon et al., Proc. Natl. Acad. Sci. 89:9367-71 discloses a polymer consisting of N-substituted glycines ("peptoids") with diverse side chains. Zuckermann et al., 1994, J. Med. Chem. 37:2678-85 screened a library of such peptoids to obtain ligands with high affinity for the $\alpha_1$-adrenergic receptor and the $\mu$-opiate receptor. Schumacher et al, 1996, Science 271:1854-7 discloses D-peptide ligands specific for Src homology domain 3 (SH3 domain) by screening phage libraries of L-peptides against a proteins (SH3) synthesized with D-amino acids and then synthesizing a selected L-peptide using D-amino acids. Also included are aptamers (Jayasena, S. D., 1999, Clin. Chem. 45:1628-50). All such compounds can be provided as libraries encompassing a large diversity of molecules. For example, Brody et al., 1999, Mol. Diagn. 4: 381-8 describes "how hundreds to thousands of aptamers can be made in an economically feasible fashion" and used in arrays.

The mimetics of the invention also include hybrid molecules, such as peptides modified for enhanced stability, such as by acetylation, incorporation of non-natural amino acids, and other modifications that are well known to one of ordinary skill in the art.

The invention provides a method of determining the ability of a compound to inhibit NF-κB by binding at the annexin 1 binding site. Such compounds can be identified by detecting inhibition of annexin 1/NF-κB binding. In certain embodiments, the method involves the use of cells, isolated proteins or protein fragments, and actual compounds. In other embodiments, inhibitors are identified in silico. In still other embodiments, both methods are used. The invention also provides a method for identifying inhibitors of NF-κB activity by modifying known inhibitors.

In one embodiment, the method comprises contacting a test compound with NF-κB and a labeled substance that binds to the annexin 1 binding sit of NF-κB. Such substances include annexin 1 and annexin 1 peptides identified herein. polypeptides can form in the absence of the compound, and measuring the binding of the ERCC1 polypeptide with the XPA polypeptide. A compound is identified as an inhibitor of NF-κB when its presence causes a decrease in the binding of the labeled substance to NF-κB.

In another embodiment, NF-κB inhibitors that bind to the annexin 1 binding site are identified or designed in silico. Those of skill in the art will understand that a set of structure coordinates for a protein or a protein/ligand complex or a portion thereof, is a relative set of points that define a shape in three dimensions. Thus, it is possible to design a molecule that would define a similar or identical shape. According to the invention, a model shape can be predicted based on the three-dimensional structural information of NF-κB and the peptide binding motif herein described. Structure based drug design refers to the use of computer simulation to predict a conformation of a peptide, polypeptide, protein, or conformational interaction between a peptide or polypeptide, and a therapeutic compound. For example, generally, for a protein to effectively interact with a therapeutic compound, it is necessary that the three dimensional structure of the therapeutic compound assume a compatible conformation that allows the compound to bind to the protein in such a manner that a desired result is obtained upon binding. Knowledge of the three dimensional structure of at least one of the binding partners, and particularly the structural coordinates of amino acids of a ligand and its binding site enables a skilled artisan to design a therapeutic compound having such a compatible conformation. For example, knowledge of the three dimensional structure of NF-κB combined with the model structure of the tri-peptide motif provides the basis to design a therapeutic compound that binds to NF-κB and results in inhibition of its activity. Such a candidate compound can be tested for binding to NF-κB according to the methods described herein.

The present invention also provides a method for inhibiting NF-κB activity in a cell or a subject comprising providing a mimetic of annexin 1, whereby the mimetic inhibits NF-κB activity by physically associating or interacting with the NF kappa B dimer.

In another embodiment, the invention provides a method of treating a disease or condition in a mammal by administering a therapeutically effective amount of a compound of the present invention. While not intending to be bound by any particular mechanism, the diseases and conditions that may be treated by the present method include, for example, those in which reduced NF-κB activity (e.g., reduced induction of NF-κB mediated gene expression) is desirable. In one embodiment, the disease is an acute inflammatory disease. In another embodiment, the disease is a chronic inflammatory disease. In another embodiment, the disease is a neoplastic disease. In yet another embodiment, the disease is cancer.

The terms "ameliorate" and "treat" are used interchangeably and include both therapeutic and prophylactic treatment. Both terms mean decrease, suppress, attenuate, diminish, arrest, or stabilize the development or progression of a disease.

In addition, annexin 1 can affect cells relevant to the inflammatory process, such as endothelial, epithelial, mast and synovial cells.

NF-κB is a as a regulator of genes in eukaryotic cells that control cell proliferation and cell survival. Many different types of human tumors have misregulated NF-κB. In tumor cells, NF-κB is active either due to mutations in genes encoding the NF-κB transcription factors themselves or in genes that control NF-κB activity. Further, some tumor cells secrete factors that cause NF-κB to become active. Blocking NF-κB can cause tumor cells to stop proliferating, to die, or to become more sensitive to the action of anti-tumor agents. Accordingly, the annexin 1 mimetics of the invention are used for treatment of neoplastic diseases and cancer. Such diseases include cancers and neoplasms of the pancreas, colon, breast, intestinal epithelium. Non-limiting examples further include epidermoid tumors, squamous tumors, such as head and neck tumors, prostate tumors, lung tumors, including lung adenocarcinoma and small cell and non-small cell lung tumors, thyroid tumors, ovarian tumors, and liver tumors. The compositions are also used for treatment of vascularized skin cancers, including squamous cell carcinoma, basal cell carcinoma. Some non-solid tumors include leukemia, multiple myeloma and lymphoma, including Hodgkin's and non-Hodgkin's lymphoma.

NF-κB controls genes involved in inflammation, and is found to be active in many inflammatory diseases, such as atherosclerosis, inflammatory bowel disease, rheumatoid arthritis and other inflammatory joint diseases, sepsis, asthma, chronic bronchitis, and cardiovascular disease, among others. Accordingly, the compositions of the present invention can also be used to treat or prevent diseases or conditions characterized by inflammation, such as atherosclerosis, rheumatoid arthritis (RA), neovascular glaucoma, proliferative retinopathy including proliferative diabetic retinopathy, macular degeneration, and psoriasis. Other non-limiting examples are insulin-dependent and non-insulin-dependent diabetes mellitus, multiple sclerosis, myasthenia gravis, Chron's disease, inflammatory bowel disease and other inflammatory immunologic (e.g., allergy) and autoimmune diseases. The compositions are also effective to reduce or eliminate secondary consequences of acute and chronic inflammatory responses, including inflammatory response to injury, such as spinal cord injury.

Other disease manifestations of chronic inflammatory responses include neurodegenerative diseases, including Alzheimer's, amyotrophic lateral sclerosis, multiple sclerosis, Parkinson's disease, Pick's disease, and Huntington's disease, and pain. These are also amenable to treatment with such agents.

In certain embodiments, the agent may be a combination of any of the four agents discussed above, i.e., nitric oxide-donating non-steroidal anti-inflammatory compounds, traditional anti-inflammatory compounds, agents that induce redox changes, annexin 1, peptides derived from annexin 1, or expression vectors comprising nucleic acids encoding annexin 1 or peptides derived from annexin 1. In especially preferred compounds an annexin 1 inducing agent is used in conjunction with annexin 1 peptides or annexin 1 mimetics to inhibit NF-κB activity in a cell or subject.

The present invention also provides pharmaceutical compositions comprising annexin 1. In other embodiments, pharmaceutical compositions of the present invention may comprise peptides derived from annexin 1, variants, or homologues or expression vectors comprising a nucleic acid encoding annexin 1 or encoding peptides derived from annexin 1 or encoding annexin 1 peptide variants or homologues.

The present invention further provides a pharmaceutical composition comprising a mimetic of annexin, wherein said mimetic physically associates with the NF-κB dimer to inhibit NF-κB activity. In another embodiment, the composition further comprises an anti-inflammatory agent and/or a nitric oxide-donating non-steroidal anti-inflammatory compound (as discussed above).

In other embodiments, the pharmaceutical composition may further comprise an anti-inflammatory agent. The anti-inflammatory agent may be any suitable anti-inflammation agent. Preferably the agent is a corticosteroid, a glucocorticosteroid, or Dex.

In other embodiments, the pharmaceutical composition may further comprise a nitric oxide-donating non-steroidal anti-inflammatory compound as described above (with or without an anti-inflammatory compound as discussed above). In certain embodiments, the nitric oxide-donating non-steroidal anti-inflammatory compound comprises NO-ASA and annexin 1 (or peptides derived from annexin 1, annexin 1 variants or homologues or expression vectors comprising nucleic acids encoding annexin 1 or peptides derived from annexin 1), and the composition may further comprise an anti-inflammatory compound.

In certain embodiments, pharmaceutical compositions described above comprising a peptide derived from annexin 1 preferably comprises the peptide as set forth in SEQ ID NO:1, the peptide set forth in SEQ ID NO:2, the peptide as set forth in SEQ ID NO:3, the peptide set forth in SEQ ID NO:4, the peptide set forth in SEQ ID NO:5, the peptide set forth in SEQ ID NO:6, the peptide set forth in SEQ ID NO:10, the peptide set forth in SEQ ID NO:11, the peptide set forth in SEQ ID NO:12, the peptide set forth in SEQ ID NO:13, or other peptide fragments of annexin 1, as long as they maintain the ability to inhibit NF-κB activity.

Pharmaceutical compositions may be prepared as medicaments to be administered in any method suitable for the subject's condition, for example, orally, parenterally (including subcutaneous, intramuscular, and intravenous), rectally, transdermally, buccally, or nasally, or may be delivered to the eye as a liquid solution. Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches and for nasal delivery, suitable forms include aerosol delivery systems known in the art.

In addition to the NO-NSAIDS, anti-inflammatory compounds, annexin 1, peptides derived from annexin 1, annexin 1 variants or homologues or agents that induce redox changes, pharmaceutical compositions of the invention may contain one or more excipient or adjuvant. Selection of excipients and the amounts to use may be readily determined by the formulation scientist based upon experience and consideration of standard procedures and reference works in the field.

Excipients such as diluents increase the bulk of a solid pharmaceutical composition, and may make a pharmaceutical dosage form containing the composition easier for the patient and care giver to handle. Diluents for solid compositions include, but are not limited to, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, or talc.

Solid pharmaceutical compositions that are compacted into a dosage form, such as a tablet, may include, but are not limited to, excipients whose functions include, but are not limited to, helping to bind the active ingredient and other excipients together after compression, such as binders. Binders for solid pharmaceutical compositions include, but are not limited to, acacia, alginic acid, carbomer (e.g., CARBOPOL®), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, or starch.

The dissolution rate of a compacted solid pharmaceutical composition in the patient's stomach may be increased by the addition of a disintegrant to the composition. Excipients which function as disintegrants include, but are not limited to, alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), or starch.

Glidants can be added to improve the flowability of a non-compacted solid composition and to improve the accuracy of dosing. Excipients that may function as glidants include, but are not limited to, colloidal silicon dioxide, magnesium trisilicate, powdered cellulose, starch, talc, or tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Excipients that function as lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, or zinc stearate.

Flavoring agents and flavor enhancers make the dosage form more palatable to the patient. Common flavoring agents and flavor enhancers for pharmaceutical products that may be included in the composition of the invention include, but are not limited to, maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the invention, the active ingredient and any other solid excipients are suspended in a liquid carrier such as water, vegetable oil, alcohol, polyethylene glycol, propylene glycol, or glycerin. As used herein, "active ingredient" means NO-NSAIDS, anti-inflammatory compounds, annexin 1, polypeptides derived from annexin 1, annexin 1 variants or homologues and/or expression vectors comprising nucleic acids encoding annexin 1, polypeptides derived from annexin 1, annexin 1 variants or homologues.

Liquid pharmaceutical compositions may contain emulsifying agents to disperse uniformly throughout the composition an active ingredient or other excipient that is not soluble in the liquid carrier. Emulsifying agents that may be useful in liquid compositions of the invention include, but are not limited to, gelatin, egg yolk, casein, cholesterol, acacia, tragacanth, chondrus, pectin, methyl cellulose, carbomer, cetostearyl alcohol, or cetyl alcohol.

Liquid pharmaceutical compositions of the invention may also contain a viscosity enhancing agent to improve the mouth-feel of the product and/or coat the lining of the gastrointestinal tract. Such agents include, but are not limited to, acacia, alginic acid, bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, or xanthan gum.

Sweetening agents such as sorbitol, saccharin, sodium saccharin, sucrose, aspartame, fructose, mannitol, or invert sugar may be added to improve the taste.

Preservatives and chelating agents such as alcohol, sodium benzoate, butylated hydroxy toluene, butylated hydroxyanisole, or ethylenediamine tetraacetic acid may be added at levels safe for ingestion to improve storage stability.

According to the invention, a liquid composition may also contain a buffer such as gluconic acid, lactic acid, citric acid or acetic acid, sodium gluconate, sodium lactate, sodium citrate, or sodium acetate.

Generally, an effective amount of the agents described above will be determined by the age, weight and condition or severity of disease of the recipient. Dosing may be one or more times daily, or less frequently, and may be in conjunction with other compositions as described herein. It should be noted that the present invention is not limited to the dosages recited herein.

Pharmaceutical compositions of the present invention discussed above may be useful for treating cancer by inhibiting cancer cell growth or by killing cancer cells. "Inhibiting cancer cell growth" means inhibiting or slowing the growth of cancer cells, and/or killing cancer cells.

Pharmaceutical compositions of the present invention discussed above may be useful for inhibiting inflammation. "Inhibiting inflammation" also means decreasing inflammation, decreasing expression of pro-inflammatory cytokines, and/or decreasing or inhibiting the inflammation cascade.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Throughout this application, various publications are referenced. The disclosures of these publications are hereby incorporated by reference into this application in order to more fully describe the state of the art to those skilled therein as of the date of the invention described and claimed herein.

EXAMPLE 1

Induction of Annexin 1 by Anti-Inflammatory Drugs

The human pancreatic cancer cell line, BxPC-3, or the colon cancer cell line HT-29, both from ATCC (Manassas, Va.) were maintained and grown in RPMI 1640 or McCoy's 5A medium (Cellgro) supplemented with 10% fetal bovine serum (HyClone) and 1% penicillin/streptomycin (Cellgro) in a humidified incubator at 37° C. and 5% $CO_2$.

For the study of induction of annexin 1 by anti-inflammatory agents, the cells were incubated with either NO-ASA or Dex for 3 h. The cell fractions were obtained as described by Andrews and Faller (N. C. Andrews and D. V. Faller, Nucleic Acids Res. 19:2499 (1991)) with modification. Briefly, the cells were pelleted after treatment and washed three times with PBS. The cell pellets were resuspended in ice cold buffer A (10 mM HEPES, pH 7.9, 10 mM KCl, 1.5 mM $MgCl_2$, 0.5 mM DTT, 0.5 mM PMSF) with protease inhibitor cocktail (Sigma) and incubated on ice for 15 min with occasional mixing by gently tapping the tube. The cell lysates were centrifuged up to 5000 rpm for three times. The supernatants were collected as cytoplasmic extracts. Nuclear pellets were washed with buffer A and resuspended in buffer C (20 mM HEPES, pH 7.9, 450 mM NaCl, 1.5 mM $MgCl_2$, 0.2 mM EDTA, 0.5 mM DTT, 0.5 mM PMSF, 25% Glycerol) with protease inhibitor cocktail (Sigma) and incubated on ice for 30 min with occasional mixing to extract nuclear proteins.

Nuclear extracts were cleared by centrifugation (14,800 rpm for 10 min) and the supernatants were collected as nuclear extracts.

For Western blotting, the proteins from both cytoplasmic extracts and nuclear extracts were separated by SDS-polyacrylamide gel electrophoresis and transferred onto PVDF membranes (Millipore). The membranes were blocked in 5% nonfat dry milk-TBS-T (20 mM Tris-HCl, pH 7.5, 500 mM NaCl. 0.3% Tween 20) at room temperature (RT) for an hour and probed with anti-annexin 1, c-IAP-1, c-IAP-2, and TRAF-1 (Santa Cruz Biotechnology, Inc. CA), and anti-Bcl-2 antibodies (Cell Signaling Technology), in 5% nonfat dry milk-TBS-T at 4° C. overnight. The blots were washed three times with TBS-T for 5 min each wash and incubated with horseradish peroxidase-conjugated secondary antibody (Santa Cruz) in 5% nonfat dry milk-TBS-T at RT for an hour. After five washes with TBS-T, the blots were developed with the enhanced chemiluminescence system (ECL™ Western Blotting System, Amersham Biosciences) and exposed to x-ray film according to the manufacturer's instructions. Protein loading was normalized using anti-β-actin antibodies (Santa Cruz Biotechnology, Inc).

Expression of annexin 1 was induced by NO-ASA in concentration- and time-dependent manners as measured by Western blots in both BxPc-3 (FIGS. 1A and B) and HT-29 cells (FIGS. 1C and D). Similar results were obtained from cells treated with Dex (FIGS. 1E and F). In contrast, conventional aspirin and weak anti-inflammatory cortisone failed to induce the expression of annexin 1 (FIGS. 1H and 1I).

EXAMPLE 2

Induction of Annexin 1 and Inhibition of NF-κB by Corticosteroid Anti-Inflammatory Agents In the same manner as for NO-ASA, BxPC-3 cells were treated for 6 h with different corticosteroid inflammatory drugs, each at 4 µM, and tested for their ability to induce annexin 1. The relative anti-inflammatory potency is as follows: cortisol=1, cortisone=0.8, prednisone=4, triamincinolone=5, fludrocortisone=10, betamethasone=25 and Dex=25 (B. P. Schimmer and K. L.; Adrenocorticotropic hormone; Adrenocortical steroids and their synthetic analogs; inhibitors of the synthesis and actions of adrenocortical hormones. Ch. 60, pp 1649-1677, Goodman& Gilman's The Pharmacological Basis of Therapeutics $10^{th}$ ed. (2001)). NF-κB activity was measured in these cells using the TransBinding NF-κB assay kit and following the instructions of the manufacturer (Panomics). Briefly, nuclear extracts obtained as described above, were incubated for 30 min in an ELISA plate coated with NF-κB consensus DNA sequence to which p50 protein can bind. After binding, antibody against p50 was added and incubated for 1 hour, followed by HRP-conjugated antibody for 1 hour. Afterwards, luminol/enhancer solution and stable peroxide solution were added and chemoluminescence was detected using a luminometer (Bio-Rad).

The Western blot in FIG. 2A shows the induction of annexin 1 by various corticosteroids. The levels of annexin 1 increased with their relative anti-inflammatory potency, with Dex inducing annexin 1 the most. FIG. 2B demonstrates that, as the anti-inflammatory potency increases, the NF-κB activity in the treated cells decreases. FIG. 2C shows the direct correlation between the anti-inflammatory potency of the corticosteroids and the level of annexin 1, which is statistically highly significant ($R^2=0.91$, $p<0.001$)

EXAMPLE 3

Failure of NSAIDS to Induce Annexin 1 in BxPC-3 Cells

BxPC-3 cells were treated for 6 h of conventional NSAIDS each at 1 mM from the following groups: salicylic acid derivatives (ASA and salicylic acid); indole and indene acetic acids (indomethacin and sulindac); arylpropionic acids (ibuprofen and flurbiprofen); and enolic acids (piroxicam). The cells were tested for induction of annexin 1 by Western blot. FIG. 2D shows that these NSAIDs had no effect on annexin 1 expression in BxPC-3 cells.

EXAMPLE 4

The Effect of the Induction of Annexin 1 on Apoptosis, Cell Proliferation and Cell Death The growth of the cells at 24 hours was determined using the MTT assay, which was carried out according to the manufacturer's protocol (Sigma). BxPC-3 cells were seeded in a 96-well plate and cultured in RPMI 1640 medium supplemented with 10% fetal bovine serum and 1% penicillin/streptomycin, as described above. The cells were exposed to NO-ASA for 24 hours at concentrations ranging from 5 to 80 µM. MTT solution (M-0283) in an amount equal to 10% of the culture medium volume was then added to each well and the cells were incubated for 4 hours. The resulting MTT formazan crystals were dissolved by adding MTT Solvent (M-0408) directly to the culture in an amount equal to the original culture volume with gentle stirring and then quantitated by an ELISA Model 680 Microplate Reader (Biorad).

Apoptosis was determined using the Cell Death Detection ELISA$^{PLUS}$ assay kit according to the manufacturer's protocol (Roche, Indianapolis, Ind.). Briefly, the cells were treated with either NO-ASA or Dex for 3 h. Cells were harvested and washed three times with PBS. The cell pellet was resuspended with lysis buffer and incubated for 30 min at RT. Cell lysis was achieved by centrifuging at 200×g for 10 min. The ELISA assay was performed using 20 µl cell lysate and 80 µl Immunoreagent (containing 72 µl Incubation Buffer, 4 µl Anti-histone-biotin Solution, and 4 µl Anti-DNA-POD Solution) per micro-plate well. The micro-plate was covered with an adhesive foil and incubated on a shaker under gentle shaking at 200 rpm for 2 h at RT. The solution in each well was removed thoroughly by tapping and the pellets were rinsed three times with 200 µl Incubation Buffer. One hundred µl of ABTS Solution (one substrate tablet was dissolved in 5 ml Substrate Buffer) were added to each well and the plate was incubated on a plate shaker at 200 rpm until color development was sufficient for photometric analysis (approximately 10 min). One hundred µl ABTS Stop Solution were added to each well to stop the reaction. The absorbance was measured at 405 nm using the SpectraMax micro-plate reader (Molecular Devices, Sunnyvale).

To determine the role of annexin 1 in apoptosis and cell death induced by NO-ASA or Dex, annexin 1 expression was knocked-down or up-regulated by its specific siRNA or its cDNA plasmid. Briefly, annexin 1 cDNA clones (OreGen) or the PCMV6XL5 vector, as a negative control, were transiently transfected into BxPC-3 cells grown to 40-60% confluency using Lipofectamine according to the product protocol (Invitrogen). Annexin 1 specific siRNA duplexes (Santa Cruz, Calif.) and fluorescein conjugated control siRNA (Santa Cruz, Calif.) were transiently transfected into the BxPC-3 cells at 40-60% confluency using Santa Cruz Biotechnology's siRNA Transfection Reagent and siRNA Transfection Medium (Santa Cruz, Calif.) according to product protocol. NF-κB activity was subsequently measured by the TransBinding NF-κB Assay Kit and ELISA as described in Example 2. Annexin 1 was assayed by Western blot as described in Example 1.

The Western blot in FIG. 3A shows that at 8 h NO-ASA suppressed the expression of the NF-κB-dependent anti-apoptotic genes survivin, Bcl-2, c-IAP-1, c-IAP-2, and TRAF-1, thus facilitating the inhibition of proliferation (FIG. 3B) and the induction of apoptosis (FIG. 3C) and hence the anticancer and perhaps anti-inflammatory effects of this compound. FIG. 3D shows that knock-down expression of annexin 1 by its specific siRNA completely abrogated the cell apoptosis induced by either NO-ASA or Dex. FIG. 3E shows that forced expression of annexin 1 by transfecting the annexin 1 cDNA plasmid into BxPC-3 cells increased cell death by about 45% through the inhibition of NF-κB activity.

EXAMPLE 5

The Effect the Induction of Annexin 1 on NF-κB Activity

Figure 4A:
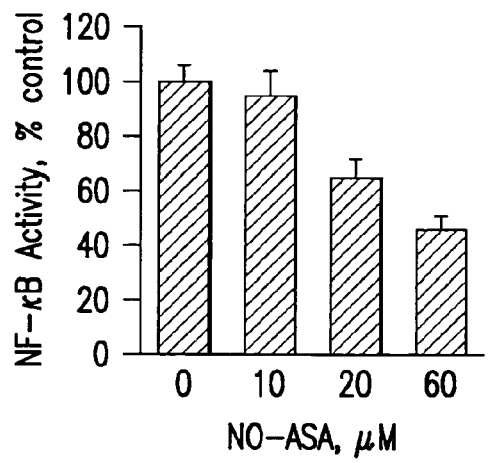
FIGS. 4A and B show NO-ASA inhibits NF-κB activity in both HT-29 and BxPC-3 cells.
Figure 4C:
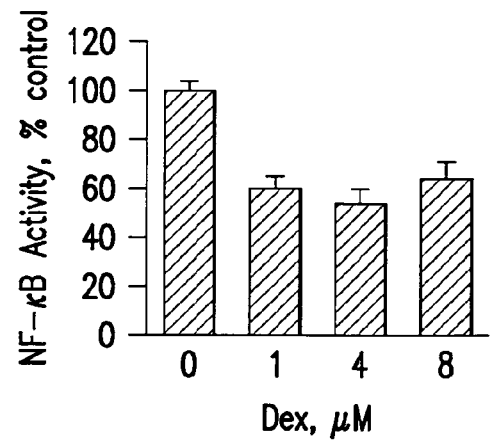
FIGS. 4C and D show that Dex inhibits NF-κB activity in both HT-29 and BxPC-3 cells.
Figure 4B:
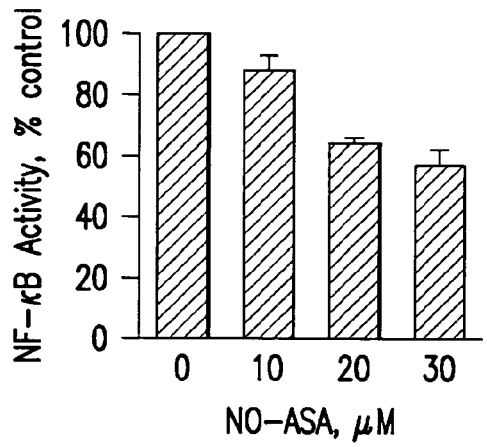
FIG. 4 shows the effect of annexin 1 on NF-κB activity.
FIG. 4E shows the effect of knock-down of annexin 1 by annexin 1-specific siRNA on NF-κB activity in BxPC-3 cells treated with NO-ASA.
Figure 4D:
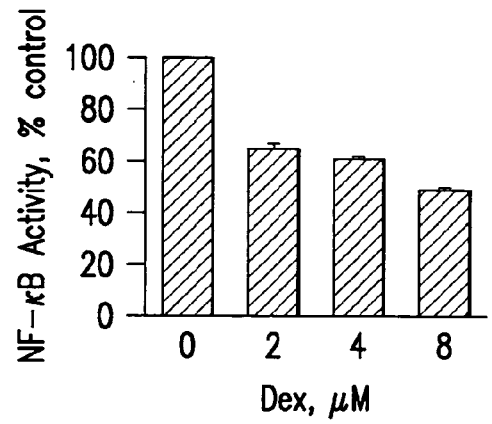
Figure 4E:
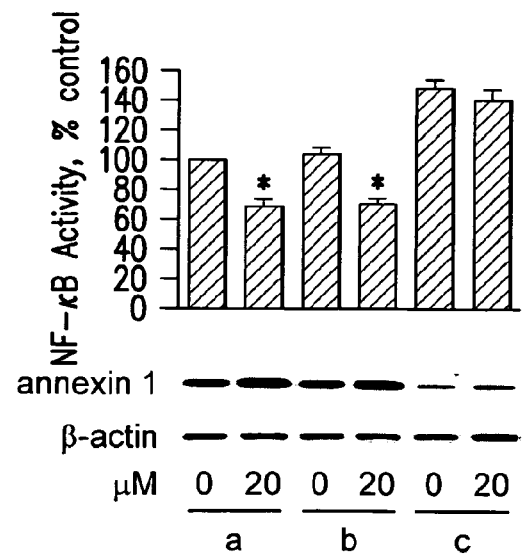

FIGS. 4A and B show that NO-ASA inhibited the activity of NF-κB in both BxPC-3 and HT-29 cells as determined at 3 h using an ELISA method. FIGS. 4C and D show that Dex inhibited NF-κB in these cells as well. FIG. 4E shows that knocking down annexin 1 expression with annexin 1-specific siRNA not only rescued cells from the inhibitory effect of NO-ASA on NF-κB activity but increased the NF-κB activity above baseline, indicating that annexin 1 may control baseline levels of NF-κB.

EXAMPLE 6

Annexin 1 is Physically Associated with NF-κB

To demonstrate that annexin 1 and NF-κB are physically associated, BxPC-3 or HT-29 cells treated with NO-ASA or Dex were fractionated and subjected to immunoprecipitation, immunoblotting and gel-shift assays.

The gel shift assays were carried out according to the manufacturer's protocol (Panomics). Nuclear proteins (10 μg) from each sample were mixed with 10 ng biotinylated p65 double-stranded oligonucleotide probes (5'-CATCG-GAAATTTCCGGAAATTTCCGGAAATTTCCGGC-3' and its complement) (SEQ ID NO:9) in the presence of 1 μg Poly(I/C) DNA. The mixture was incubated at room temperature for 30 min. The binding complex was then resolved using a 6% polyacrylamide/glycerol gel in 0.5% Tris-borate-EDTA, transferred onto a nylon membrane, and fixed on the membrane by UV cross-linking The biotin-labeled probe was detected with streptavidin-horseradish peroxidase. Co-immunoprecipitation was performed as follows: about 500 μg of cell extracts were incubated overnight with 5 μg of agarose-conjugated anti-p65 (Santa Cruz Biotechnology) or anti-annexin 1 antibody (Santa Cruz, Calif.). The precipitate was washed five times with washing buffer (Santa Cruz Biotechnology), dissolved in 2× Laemmli buffer, boiled, and separated by SDS-PAGE and detected by Western blot analysis using ECL™ (Amersham Biosciences) as described above. Control experiments were performed by using rabbit IgG for p65 and mouse IgG2b for annexin 1, respectively (Santa Cruz Biotechnology).

Nuclear proteins extracted from BxPC-3 cells treated for 3 h with or without NO-ASA (20 μM) were reacted with κB double-stranded oligomers (SEQ ID NO:9) immobilized in reaction wells (Panomics). NF-κB dimers that bound to the κB oligomers (SEQ ID NO:9) were recognized by anti-p65 or anti-p50 antibodies through a color reaction. An anti-annexin 1 mAb that did not cross-react with either p50 or p65 generated a positive reaction. FIG. 5A shows that NF-κB binding to its DNA-recognition sequence (SEQ ID NO:9) was identified using anti-p50, anti-p65 (both identifying NF-κB) and anti-annexin 1 antibodies. FIGS. 5B and C show the results of immunoprecipitation (IP) of the p65 subunit of NF-κB from whole cell lysates of BxPC-3 (FIG. 5B) and HT-29 (FIG. 5C) cells treated with NO-ASA or Dex for 3 h. Subsequent immunoblots (IB) with anti-annexin 1 mAb revealed that annexin 1 co-immunoprecipitated with p65 only in NO-ASA or Dex treated cells; p65 was precipitated in both treated and untreated cells (top two panels). A nonspecific antibody (bottom two panels) failed to co-immunoprecipitate annexin 1. FIG. 5D provides the results of an EMSA from BxPC-3 cells treated with NO-ASA for 3 h. The NO-ASA-treated BxPC-3 nuclear extract was reacted with or without anti-annexin 1 or non-specific IgG prior to its reaction with the κB probe. The left panel shows that NO-ASA inhibited the binding of NF-κB to the DNA probe in a concentration-dependent manner, with substantial suppression of binding at 20 μM NO-ASA. When the nuclear extract was reacted with anti-annexin 1 mAb for 30 min at room temperature prior to being reacted with the κB oligomer, binding of NF-κB to its DNA recognition sequence (the double-stranded κB oligomer, SEQ ID NO:9) was restored, as shown in the right panel of FIG. 5D.

EXAMPLE 7

Annexin 1 Co-Localizes with NF-κB p65 in NO-ASA or Dex-Treated BxPC-3 Cells

BxPC-3 cells were seeded on cover-glasses in a 12-well plate for 24 h. The cells were exposed to 10 or 20 μM NO-ASA or 2 or 4 μM Dex for 3 h, fixed with 4% paraformaldehyde in PBS containing 30 mM sucrose, permeabilized with 0.2% saponin in PBS containing 30 mM sucrose, and blocked with 5% normal goat serum in PBS containing 1% BSA. The cells were incubated with mouse monoclonal IgG2b anti-annexin 1 (Santa Cruz Biotechnology) and rabbit monoclonal IgG anti-p65 (Cell Signaling, MA) at RT for 1 h. After three washes with PBS containing 1% BSA, the cells were incubated with Alexa555 conjugated donkey anti-mouse IgG (Molecular Probes) and Alexa 488 conjugated goat anti-rabbit IgG (Molecular Probes) at RT for an hour. Images were acquired with a Zeiss LSM 510 META NLO Two-Photon Laser Scanning Image Confocal Microscope and the colocalization scores were generated by the Colocalization Macro program. The control experiments were performed using non-specific mouse IgG2b and/or rabbit IgG. Red fluorescence localized annexin 1, green fluorescence localized p65 (NF-κB) and co-localization of the two proteins generated yellow fluorescence. This is demonstrated in FIG. 6. Each score graph panel shows the fluorescent intensity of free p65 (a), free annexin 1 (b), and of both when co-localized (c).

Figure 6A:
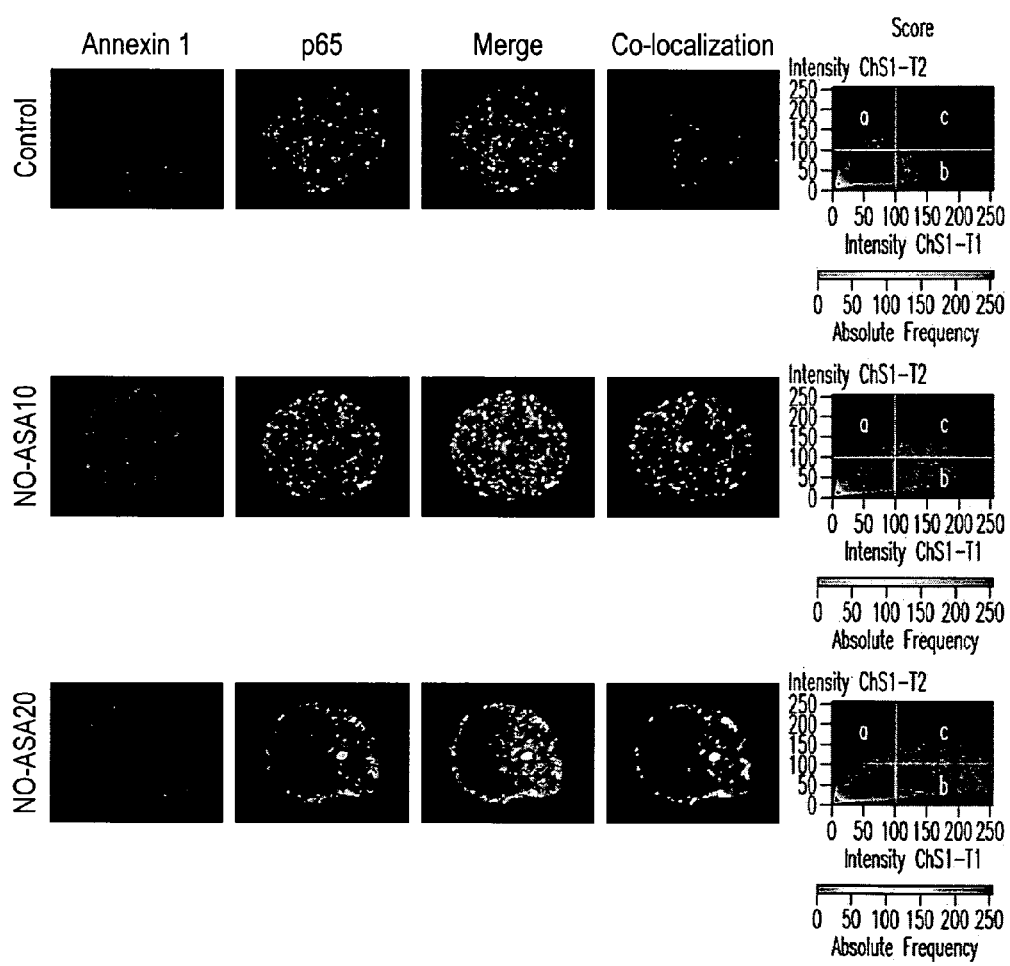
FIG. 6A shows the colocalization of annexin 1 and NF-κB p65 in BxPC-3 cells treated with NO-ASA.
Figure 6B:
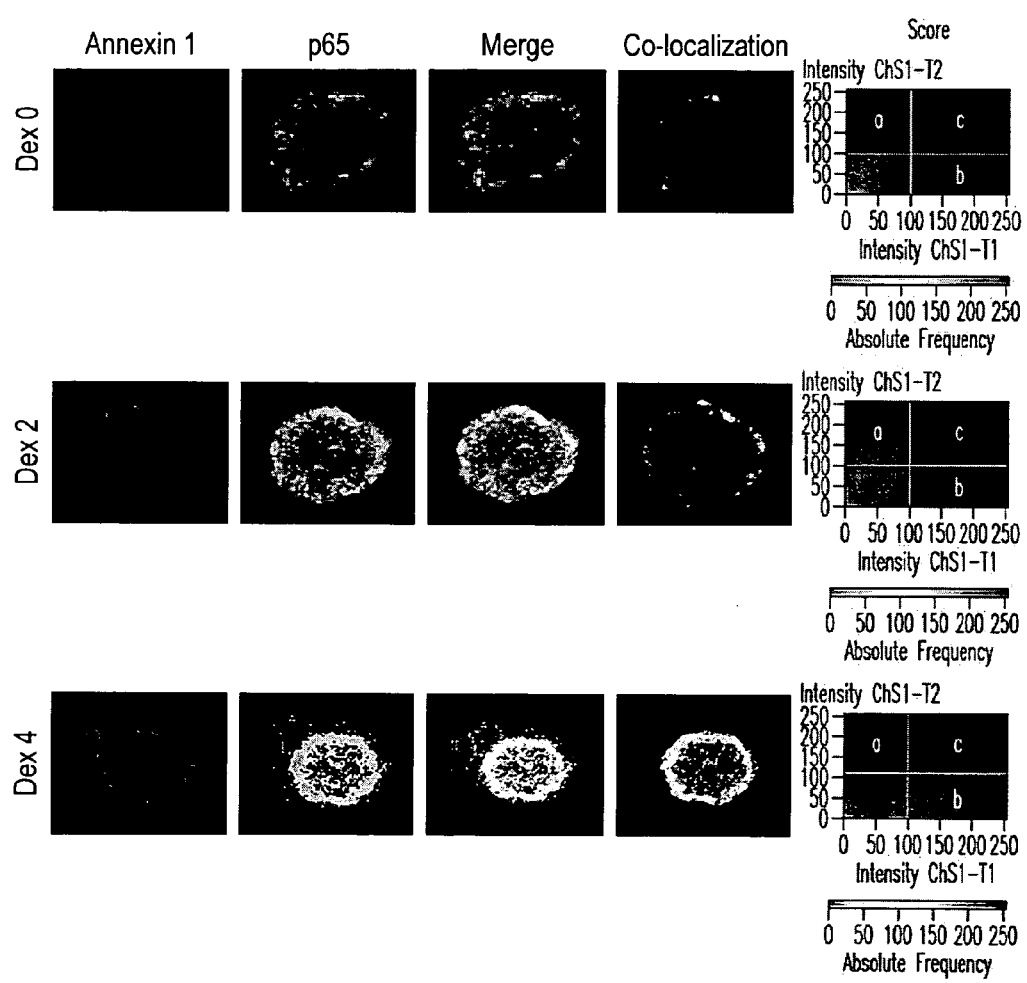
FIG. 6B shows the colocalization of annexin 1 and NF-κB p65 in BxPC-3 cells treated with Dex.

FIG. 6A shows the fluorescence of NO-ASA-treated BxPC-3 cells. The annexin 1 and p65 co-localize most strongly in the nucleus of cells treated with NO-ASA 20 μM, designated NO-ASA20 in the Figure. FIG. 6B shows the results of Dex-treated cells, where the co-localization of annexin 1 and p65 staining also appeared in the nucleus of Dex4-treated BxPC-3 cells.

EXAMPLE 8

Co-Localization of Annexin 1 and NF-κB p65 in NO-ASA-Treated Mice

A mouse model of multiple intestinal neoplasia, the Min mice, and the congenic parent wild-type mice were used to test the in vivo action of NO-ASA in the induction of annexin 1. Both wild-type and Min mice were treated for 7 days with vehicle or NO-ASA 100 mg/kg. After 7 days of treatment, the mice were sacrificed and the epithelial cells were evaluated as in Example 6 by confocal microscopy. FIG. 8C shows that the co-localization of annexin 1 and p65 was only found in the nucleus of epithelial cells from NO-ASA-treated Min mice.

EXAMPLE 9

The Induction of Annexin 1 by NO-ASA or Dex Inhibits NF-κB in an Animal Model of Cancer FIGS. 7A and 8A show the induction of annexin 1 in NO-ASA or Dex-treated wild-type and Min mice as described in EXAMPLE 8. FIGS. 7B and 8B show that both NO-ASA and Dex inhibited NF-κB activity in wild-type and Min mice. FIG. 7C shows that the induced annexin 1 physically bound to NF-κB p65 in both wild-type mice and Min mice. FIGS. 7D and E show that NO-ASA and Dex inhibited NF-κB dependent gene expression, leading to apoptosis.

EXAMPLE 10

Peptides of Annexin 1 Inhibit NF-κB Activity and Promote Apoptosis

BxPC-3 or SW480 cells were treated with 30 μM of each of the peptides of annexin 1 for 3 h. NF-κB activity and apoptosis were measured in whole cell lysates using an ELISA assay as described in EXAMPLES 2 and 4. FIG. 9A shows that the commercial peptides of annexin 1 (SEQ ID NO:7), Ac2-26 (SEQ ID NO:10) and Ac2-12 (SEQ ID NO:12) inhibited NF-κB activity in BxPC-3 cells. FIG. 9B shows that the synthetic peptides prepared by the inventors inhibited NF-κB activity in those cells as well. These peptides are Ac-Gln-Ala-Trp, as set forth in SEQ ID NO:1, the peptide Ac-Phe-Gln-Ala-Tip, as set forth in SEQ ID NO:2 and the peptide Ac-Phe-Leu-Lys-Gln-Ala-Trp, as set forth in SEQ ID NO:3. Other depicted acetylated peptides are Ac-Phe-Leu-Lys (SEQ ID NO:14), Ac-Lys-Gln-Ala-Trp (SEQ ID NO:15), and Ac-Val-Ser-Glu-Lys-Gln-Ala-Trp (SEQ ID NO:16).

Figure 9C:
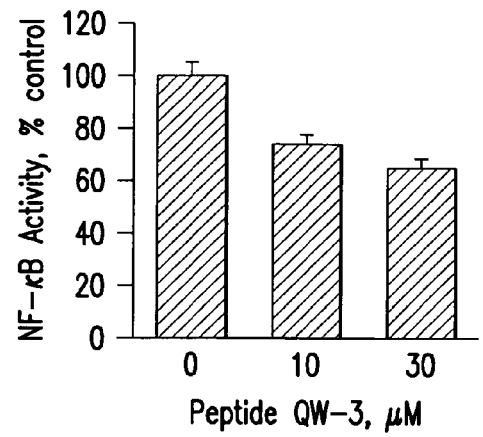
FIGS. 9C and D show that the synthetic peptide of annexin 1, QW-3 (SEQ ID NO:1) inhibits NF-κB in human colon cancer cells.
Figure 9B:
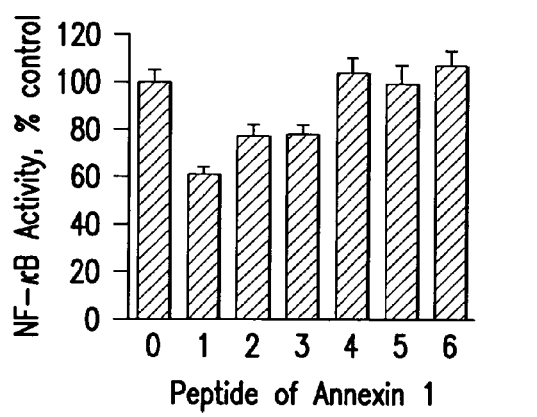
FIG. 9B shows that three of six synthetic peptides of annexin 1, Ac-Gln-Ala-Trp (SEQ ID NO:1), Ac-Phe-Gln-Ala-Trp (SEQ ID NO:2), and Ac-Phe-Leu-Lys-Gln-Ala-Trp (SEQ ID NO:3) inhibit NF-κB activity in BxPC-3 cells. Other depicted acetylated peptides are Ac-Phe-Leu-Lys (SEQ ID NO:14), Ac-Lys-Gln-Ala-Trp (SEQ ID NO:15), and Ac-Val-Ser-Glu-Lys-Gln-Ala-Trp (SEQ ID NO:16).
Figure 9D:
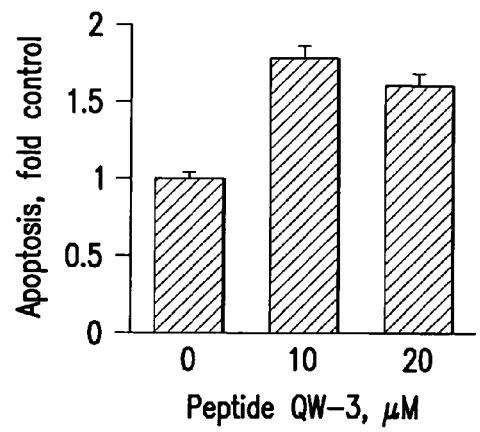
FIG. 9 shows the effect of peptides of annexin 1 on NF-κB activity and apoptosis in human cancer cells.

The peptide QW-3, Ac-Gln-Ala-Trp (SEQ ID NO:1) inhibited NF-κB activity in a concentration-dependent manner in SW480 human colon cancer cells as shown in FIG. 9C. FIG. 9D shows that the QW-3 peptide enhanced SW480 cell apoptosis.

EXAMPLE 11

QW-3 Inhibits Tumor Growth, Cell Proliferation, and Inflammation in a Human Colon Cancer Xenograft of Nude Mice Via the Inhibition of NF-κB Activity Female 6-week-old BALB/c nude mice were obtained from The Jackson Laboratory (Bar Harbor, Me.). The animals were housed in a climate- and light-controlled room. Food and water were allowed ad libitum. The SW480 human colon cancer cell line was used to establish xenografts in nude mice. $2 \times 10^6$ cells in 100 μl of PBS were injected subcutaneously (s.c.) into the upper portion of the left hind limb of the mice, where they grew as solid tumors. The size of the tumor was measured two times per week using a Venier caliper. The tumor volume was determined using the formula $V=L \times W(L+W/2) \times 0.56$.

On the $7^{th}$ day after inoculation, when the tumor size reached an average 240 mm³, 18 mice were treated with QW-3 administered by i.p. injection of at a dose of 40 μg once daily. The control group (n=18) was administered the vehicle alone. The mice were sacrificed on day 12, and tumors were resected and stored in liquid nitrogen and formalin until further analysis.

Immunohistochemistry was performed on paraffin sections of the tumors. All sections were incubated at 95-100° C. in WCAP reagent (Surgipath) for 30 min, washed and then incubated in 10:1 Methanol:$H_2O_2$ for 10 min. Sections were then incubated in rabbit polyclonal PCNA (Santa Cruz, Calif.) or antibody detecting NF-κB activation (Chemicon) for 1 h after which immunoreactivity was detected with an Envision assay kit and DAB reagent (DakoCytomation). All sections were counterstained with haematoxylin and mounted. Negative controls included a non-specific antibody.

Figure 10B:
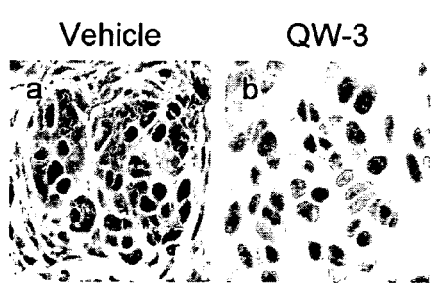
FIG. 10B shows that QW-3 reduces tumor cell proliferation.
Figure 10D:
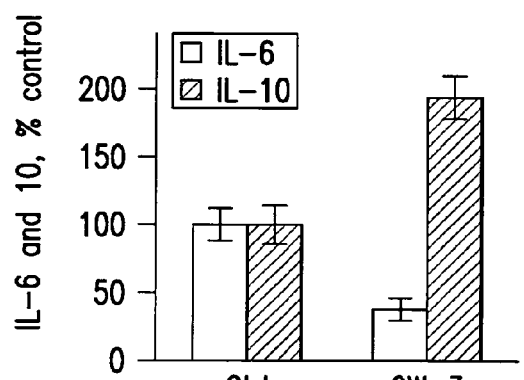
FIG. 10D shows that QW-3 decreases the blood levels of IL-6 and increases those levels of IL-10.

FIG. 10A shows that QW-3 suppressed tumor growth. The tumors in mice treated with QW-3 did not grow, and regressed, while the tumors in the untreated animals grew large. The immunohistochemistry images in FIG. 10B show that QW-3 inhibited cell proliferation by the expression of PCNA, a marker for cell proliferation, in nuclei (as evidenced in by lack of staining) FIG. 10C shows that QW-3 inhibited NF-κB activity. FIG. 10D shows that QW-3 also increased the blood levels of IL-10, an anti-inflammatory cytokine, and decreased levels of IL-6, a pro-inflammatory cytokine. The data shown are mean values per group±SD. The difference between the control group and the treated group was negligible, but in the peptide QW-3 treated group, the difference it is highly significant (p<0.001), indicating that this short peptide of annexin 1 suppresses inflammation.

The invention claimed is:
1. A method of inhibiting NF-κB in a cell comprising providing to the cell a peptide consisting of SEQ ID NO:1, SEQ ID NO:2, SEQ ID NO:3, SEQ ID NO:4, or SEQ ID NO:5.
2. The method of claim 1, wherein the peptide consists of SEQ ID NO:1.
3. The method of claim 1, wherein the peptide consists of SEQ ID NO:4.
4. The method of claim 1, wherein the peptide consists of SEQ ID NO:5.
5. A method of inhibiting NF-κB in a subject comprising administering to the subject a peptide consisting of SEQ ID NO:1, SEQ ID NO:2, SEQ ID NO:3, SEQ ID NO:4, SEQ ID NO:5 or SEQ ID NO:6.
6. The method of claim 5, wherein the peptide consists of SEQ ID NO:1.
7. The method of claim 5, wherein the peptide consists of SEQ ID NO:4.
8. The method of claim 5, wherein the peptide consists of SEQ ID NO:5.
9. The method of claim 5, wherein administering the peptide comprises providing an expression vector comprising a nucleic acid encoding said peptide, wherein said expression vector is capable of expressing said peptide.
10. The method of claim 9, wherein said peptide consists of SEQ ID NO:4.
11. The method of claim 9, wherein said peptide consists of SEQ ID NO:5.
12. The method of claim 9, wherein said peptide consists of SEQ ID NO:6.
13. The method of claim 9, wherein said expression vector is provided to a suitable cell.
14. A method of treating a neoplastic disease in a subject in need thereof, comprising administering to the subject annexin 1 or an annexin 1 mimetic in an amount effective to inhibit NF-κB, and further comprising administering a non-steroidal agent or providing a condition, wherein said agent or condition is capable of inducing annexin 1 expression.
15. A method of inhibiting NF-κB in a cell comprising providing to the cell an annexin 1 mimetic comprising SEQ ID NO:1, SEQ ID NO:2, or SEQ ID NO:3.
16. The method of claim 5, wherein the peptide consists of SEQ ID NO:2.
17. The method of claim 5, wherein the peptide consists of SEQ ID NO:3.
18. The method of claim 5, wherein the peptide consists of SEQ ID NO:6.
19. A method of inhibiting NF-κB in a subject comprising administering to the subject an annexin 1 mimetic comprising SEQ ID NO:1, SEQ ID NO:2, or SEQ ID NO:3.
20. The method of any one of claims 5-8 and 15-19, further comprising administering a non-steroidal agent or providing a condition, wherein said agent or condition is capable of inducing annexin 1 expression.
21. The method of claim 20, wherein the non-steroidal agent is administered, which is a nitric oxide-donating non-steroidal anti-inflammatory compound (NO-NSAID).
22. The method of claim 21, wherein the NO-NSAID is a nitric oxide-donating salicylic acid derivative, a nitric oxide-donating indole acetic acid, a nitric oxide-donating indene acetic acid, a nitric oxide-donating arylpropionic acid, or a nitric oxide-donating enolic acid.
23. The method of claim 22, wherein the NO-NSAID is nitric oxide-donating aspirin (NO-ASA).
24. The method of claim 20, wherein the condition is provided which induces redox changes and/or oxidative stress in a target cell or in the subject, wherein said condition induces expression of annexin 1.
25. The method of claim 1, wherein the peptide consists of SEQ ID NO:2.
26. The method of claim 1, wherein the peptide is consists of SEQ ID NO:3.
27. A method of inhibiting NF-κB in a subject comprising administering to the subject annexin 1 or an annexin 1 mimetic peptide and a non-steroidal agent capable of inducing annexin 1 expression.
28. The method of claim 27, wherein the annexin 1 mimetic peptide comprises SEQ ID NO:1, SEQ ID NO:2, SEQ ID NO:3, SEQ ID NO:4, SEQ ID NO:5 or SEQ ID NO:6.
29. The method of claim 27, wherein the annexin 1 mimetic peptide consists of SEQ ID NO:1, SEQ ID NO:2, SEQ ID NO:3, SEQ ID NO:4, SEQ ID NO:5 or SEQ ID NO:6.
30. The method of claim 27, wherein the non-steroidal agent is a nitric oxide-donating non-steroidal anti-inflammatory compound (NO-NSAID).
31. The method of claim 30, wherein the NO-NSAID is a nitric oxide-donating salicylic acid derivative, a nitric oxide-donating indole acetic acid, a nitric oxide-donating indene acetic acid, a nitric oxide-donating arylpropionic acid, or a nitric oxide-donating enolic acid.
32. The method of claim 30, wherein the NO-NSAID is nitric oxide-donating aspirin (NO-ASA).
33. The method of claim 14, which comprises administering a peptide which consists of SEQ ID NO:1.
34. The method of claim 14, which comprises administering a peptide which consists of SEQ ID NO:2.
35. The method of claim 14, which comprises administering a peptide which consists of SEQ ID NO:3.
36. The method of claim 14, which comprises administering a peptide which consists of SEQ ID NO:4.
37. The method of claim 14, which comprises administering a peptide which consists of SEQ ID NO:5.
38. The method of claim 14, which comprises administering a peptide which consists of SEQ ID NO:6.
39. The method of claim 14, which comprises administering an annexin 1 mimetic which comprises SEQ ID NO:1.
40. The method of claim 14, which comprises administering an annexin 1 mimetic which comprises SEQ ID NO:2.
41. The method of claim 14, which comprises administering an annexin 1 mimetic which comprises SEQ ID NO:3.
42. The method of claim 14, which comprises administering an annexin 1 mimetic which comprises SEQ ID NO:4.
43. The method of claim 14, which comprises administering an annexin 1 kjikmimetic which comprises SEQ ID NO:5.
44. The method of claim 14, which comprises administering an annexin 1 mimetic which comprises SEQ ID NO:6.
45. The method of any one of claims 14 and 33-44, wherein the non-steroidal agent is administered which is a nitric oxide-donating non-steroidal anti-inflammatory compound (NO-NSAID).
46. The method of claim 45, wherein the NO-NSAID is a nitric oxide-donating salicylic acid derivative, a nitric oxide-donating indole acetic acid, a nitric oxide-donating indene acetic acid, a nitric oxide-donating arylpropionic acid, or a nitric oxide-donating enolic acid.
47. The method of claim 46, wherein the NO-NSAID is nitric oxide-donating aspirin (NO-ASA).
48. The method of claim 45, wherein the condition is provided which induces redox changes and/or oxidative stress in a target cell or in the subject, wherein said condition induces expression of annexin 1.
49. A method of treating a neoplastic disease in a subject in need thereof, comprising administering to the subject an annexin 1 mimetic peptide in an amount effective to inhibit NF-κB, wherein the annexin 1 mimetic peptide comprises SEQ ID NO:1, SEQ ID NO:2, or SEQ ID NO:3.

50. A method of treating a neoplastic disease in a subject in need thereof, comprising administering to the subject an amount of a peptide effective to inhibit NF-κB, wherein the peptide consists of SEQ ID NO:1, SEQ ID NO:2, SEQ ID NO:3, SEQ ID NO:4, SEQ ID NO:5, or SEQ ID NO:6.

51. The method of claim 50, wherein the peptide consists of SEQ ID NO:1.

52. The method of claim 50, wherein the peptide consists of SEQ ID NO:2.

53. The method of claim 50, wherein the peptide consists of SEQ ID NO:3.

54. The method of claim 50, wherein the peptide consists of SEQ ID NO:4.

55. The method of claim 50, wherein the peptide consists of SEQ ID NO:5.

56. The method of claim 50, wherein the peptide consists of SEQ ID NO:6.

* * * * *

UNITED STATES PATENT AND TRADEMARK OFFICE
CERTIFICATE OF CORRECTION

PATENT NO.        : 8,691,764 B2
APPLICATION NO.   : 12/593550
DATED             : April 8, 2014
INVENTOR(S)       : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1025 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 16

<210> SEQ ID NO 1
<211> LENGTH: 3
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (1)..(1)
```

<223> OTHER INFORMATION: ACETYLATION

<400> SEQUENCE: 1

Gln Ala Trp
1

<210> SEQ ID NO 2
<211> LENGTH: 4
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 2

Phe Gln Ala Trp
1

<210> SEQ ID NO 3
<211> LENGTH: 6
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 3

Phe Leu Lys Gln Ala Trp
1               5

<210> SEQ ID NO 4
<211> LENGTH: 3
<212> TYPE: PRT
<213> ORGANISM: unknown
<220> FEATURE:
<223> OTHER INFORMATION: synthetic

<400> SEQUENCE: 4

Gln Ala Trp
1

<210> SEQ ID NO 5
<211> LENGTH: 4
<212> TYPE: PRT
<213> ORGANISM: unknown
<220> FEATURE:
<223> OTHER INFORMATION: synthetic

<400> SEQUENCE: 5

Phe Gln Ala Trp
1

<210> SEQ ID NO 6
<211> LENGTH: 6
<212> TYPE: PRT
<213> ORGANISM: unknown
<220> FEATURE:
<223> OTHER INFORMATION: synthetic

<400> SEQUENCE: 6

Phe Leu Lys Gln Ala Trp
1               5

<210> SEQ ID NO 7
<211> LENGTH: 1399
<212> TYPE: DNA
<213> ORGANISM: Homo sapiens
<220> FEATURE:
<221> NAME/KEY: CDS
<222> LOCATION: (75)..(1115)

<400> SEQUENCE: 7

| | |
|---|---|
| agtgtgaaat cttcagagaa gaatttctct ttagttcttt gcaagaaggt agagataaag | 60 |
| acactttttc aaaa atg gca atg gta tca gaa ttc ctc aag cag gcc tgg<br>                Met Ala Met Val Ser Glu Phe Leu Lys Gln Ala Trp<br>                 1                 5                    10 | 110 |
| ttt att gaa aat gaa gag cag gaa tat gtt caa act gtg aag tca tcc<br>Phe Ile Glu Asn Glu Glu Gln Glu Tyr Val Gln Thr Val Lys Ser Ser<br>      15                 20                   25 | 158 |
| aaa ggt ggt ccc gga tca gcg gtg agc ccc tat cct acc ttc aat cca<br>Lys Gly Gly Pro Gly Ser Ala Val Ser Pro Tyr Pro Thr Phe Asn Pro<br> 30                 35                    40 | 206 |
| tcc tcg gat gtc gct gcc ttg cat aag gcc ata atg gtt aaa ggt gtg<br>Ser Ser Asp Val Ala Ala Leu His Lys Ala Ile Met Val Lys Gly Val<br>45                  50                    55                    60 | 254 |
| gat gaa gca acc atc att gac att cta act aag cga aac aat gca cag<br>Asp Glu Ala Thr Ile Ile Asp Ile Leu Thr Lys Arg Asn Asn Ala Gln<br>                65                    70                    75 | 302 |
| cgt caa cag atc aaa gca gca tat ctc cag gaa aca gga aag ccc ctg<br>Arg Gln Gln Ile Lys Ala Ala Tyr Leu Gln Glu Thr Gly Lys Pro Leu<br>                    80                    85                    90 | 350 |
| gat gaa aca ctt aag aaa gcc ctt aca ggt cac ctt gag gag gtt gtt<br>Asp Glu Thr Leu Lys Lys Ala Leu Thr Gly His Leu Glu Glu Val Val<br>                95                    100                  105 | 398 |
| tta gct ctg cta aaa act cca gcg caa ttt gat gct gat gaa ctt cgt<br>Leu Ala Leu Leu Lys Thr Pro Ala Gln Phe Asp Ala Asp Glu Leu Arg<br>        110                   115                  120 | 446 |
| gct gcc atg aag ggc ctt gga act gat gaa gat act cta att gag att<br>Ala Ala Met Lys Gly Leu Gly Thr Asp Glu Asp Thr Leu Ile Glu Ile<br>125                 130                  135                  140 | 494 |
| ttg gca tca aga act aac aaa gaa atc aga gac att aac agg gtc tac<br>Leu Ala Ser Arg Thr Asn Lys Glu Ile Arg Asp Ile Asn Arg Val Tyr<br>                    145                  150                  155 | 542 |
| aga gag gaa ctg aag aga gat ctg gcc aaa gac ata acc tca gac aca<br>Arg Glu Glu Leu Lys Arg Asp Leu Ala Lys Asp Ile Thr Ser Asp Thr<br>                160                  165                  170 | 590 |
| tct gga gat ttt cgg aac gct ttg ctt tct ctt gct aag ggt gac cga<br>Ser Gly Asp Phe Arg Asn Ala Leu Leu Ser Leu Ala Lys Gly Asp Arg<br>175                 180                  185 | 638 |
| tct gag gac ttt ggt gtg aat gaa gac ttg gct gat tca gat gcc agg<br>Ser Glu Asp Phe Gly Val Asn Glu Asp Leu Ala Asp Ser Asp Ala Arg<br>        190               195                  200 | 686 |
| gcc ttg tat gaa gca gga gaa agg aga aag ggg aca gac gta aac gtg<br>Ala Leu Tyr Glu Ala Gly Glu Arg Arg Lys Gly Thr Asp Val Asn Val<br>205                 210                  215                  220 | 734 |
| ttc aat acc atc ctt acc acc aga agc tat cca caa ctt cgc aga gtg<br>Phe Asn Thr Ile Leu Thr Thr Arg Ser Tyr Pro Gln Leu Arg Arg Val<br>                    225                  230                  235 | 782 |
| ttt cag aaa tac acc aag tac agt aag cat gac atg aac aaa gtt ctg<br>Phe Gln Lys Tyr Thr Lys Tyr Ser Lys His Asp Met Asn Lys Val Leu<br>                240                  245                  250 | 830 |
| gac ctg gag ttg aaa ggt gac att gag aaa tgc ctc aca gct atc gtg<br>Asp Leu Glu Leu Lys Gly Asp Ile Glu Lys Cys Leu Thr Ala Ile Val<br>255                 260                  265 | 878 |

```
aag tgc gcc aca agc aaa cca gct ttc ttt gca gag aag ctt cat caa      926
Lys Cys Ala Thr Ser Lys Pro Ala Phe Phe Ala Glu Lys Leu His Gln
    270                 275                 280 gcc atg aaa ggt gtt gga act cgc cat aag gca ttg atc agg att atg      974
Ala Met Lys Gly Val Gly Thr Arg His Lys Ala Leu Ile Arg Ile Met
285                 290                 295                 300 gtt tcc cgt tct gaa att gac atg aat gat atc aaa gca ttc tat cag     1022
Val Ser Arg Ser Glu Ile Asp Met Asn Asp Ile Lys Ala Phe Tyr Gln
                305                 310                 315 aag atg tat ggt atc tcc ctt tgc caa gcc atc ctg gat gaa acc aaa     1070
Lys Met Tyr Gly Ile Ser Leu Cys Gln Ala Ile Leu Asp Glu Thr Lys
                320                 325                 330 gga gat tat gag aaa atc ctg gtg gct ctt tgt gga gga aac taa         1115
Gly Asp Tyr Glu Lys Ile Leu Val Ala Leu Cys Gly Gly Asn
                335                 340                 345 acattccctt gatggtctca agctatgatc agaagacttt aattatatat tttcatccta   1175
taagcttaaa taggaaagtt tcttcaacag gattacagtg tagctaccta catgctgaaa   1235
aatatagcct ttaaatcatt tttatattat aactctgtat aatagagata agtccattt   1295

taaaaatgt tttccccaaa ccataaaacc ctatacaagt tgttctagta acaatacatg   1355
agaaagatgt ctatgtagct gaaaataaaa tgacgtcaca agac                    1399

<210> SEQ ID NO 8
<211> LENGTH: 346
<212> TYPE: PRT
<213> ORGANISM: Homo sapiens

<400> SEQUENCE: 8

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
        50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205
```

```
Ala Gly Glu Arg Arg Lys Gly Thr Asp Val Asn Val Phe Asn Thr Ile
        210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 9
<211> LENGTH: 37
<212> TYPE: DNA
<213> ORGANISM: unknown
<220> FEATURE:
<223> OTHER INFORMATION: synthetic

<400> SEQUENCE: 9
catcggaaat tccggaaat tccggaaat ttccggc                         37

<210> SEQ ID NO 10
<211> LENGTH: 25
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 10

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25

<210> SEQ ID NO 11
<211> LENGTH: 25
<212> TYPE: PRT
<213> ORGANISM: unknown
<220> FEATURE:
<223> OTHER INFORMATION: synthetic

<400> SEQUENCE: 11

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25

<210> SEQ ID NO 12
```

```
<211> LENGTH: 11
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 12

Ala Met Val Ser Glu Phe Leu Lys Gln Ala Trp
1               5                   10

<210> SEQ ID NO 13
<211> LENGTH: 11
<212> TYPE: PRT
<213> ORGANISM: unknown
<220> FEATURE:
<223> OTHER INFORMATION: synthetic

<400> SEQUENCE: 13

Ala Met Val Ser Glu Phe Leu Lys Gln Ala Trp
1               5                   10

<210> SEQ ID NO 14
<211> LENGTH: 3
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 14

Phe Leu Lys
1

<210> SEQ ID NO 15
<211> LENGTH: 4
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 15

Lys Gln Ala Trp
1

<210> SEQ ID NO 16
<211> LENGTH: 7
<212> TYPE: PRT
<213> ORGANISM: unknown
<220> FEATURE:
<223> OTHER INFORMATION: synthetic
<220> FEATURE:
<221> NAME/KEY: MOD_RES
<222> LOCATION: (1)..(1)
<223> OTHER INFORMATION: ACETYLATION

<400> SEQUENCE: 16

Val Ser Glu Lys Gln Ala Trp
1               5
```